(12) United States Patent
Madder et al.

(10) Patent No.: US 10,753,944 B2
(45) Date of Patent: Aug. 25, 2020

(54) METHODS FOR COVALENTLY BINDING A CELL SURFACE PROTEIN AND A LIGAND

(71) Applicant: UNIVERSITEIT GENT, Ghent (BE)

(72) Inventors: Annemieke Madder, Massemen (BE); Christophe Ampe, Ghent (BE); Willem Vannecke, Sint-Denijs-Westrem (BE); Marleen Van Troys, Deinze (BE)

(73) Assignee: UNIVERSITEIT GENT, Ghent (BE)

( * ) Notice: Subject to any disclaimer, the term of this patent is extended or adjusted under 35 U.S.C. 154(b) by 0 days.

(21) Appl. No.: 16/081,030

(22) PCT Filed: Mar. 1, 2017

(86) PCT No.: PCT/EP2017/054708
§ 371 (c)(1),
(2) Date: Aug. 29, 2018

(87) PCT Pub. No.: WO2017/148979
PCT Pub. Date: Sep. 8, 2017

(65) Prior Publication Data
US 2019/0064176 A1 Feb. 28, 2019

(30) Foreign Application Priority Data
Mar. 1, 2016 (EP) .................................... 16158059

(51) Int. Cl.
*A61K 38/00* (2006.01)
*G01N 33/68* (2006.01)

(52) U.S. Cl.
CPC ... *G01N 33/6842* (2013.01); *G01N 2333/705* (2013.01)

(58) Field of Classification Search
None
See application file for complete search history.

(56) References Cited

U.S. PATENT DOCUMENTS

| | | | | | |
|---|---|---|---|---|---|
| 6,087,115 | A | * | 7/2000 | Gershengorn | C07K 14/723 435/252.3 |
| 2008/0260744 | A1 | * | 10/2008 | Gaitanaris | C07K 14/723 424/139.1 |
| 2013/0289239 | A1 | * | 10/2013 | Madded | C07K 1/1075 530/328 |

FOREIGN PATENT DOCUMENTS

WO  2012/085279 A2  6/2012

OTHER PUBLICATIONS

Prakasam et al., Jul. 2013, "Click Chemistry for Drug Development and Diverse Chemical—Biology Applications", Chemical Reviews, vol. 113, No. 7, pp. 4905-4979.
Carrette et al., Jan. 2016, "Furan oxidation based cross-linking: a new approach for the study and targeting of nucleic acid and protein interactions", Chemical Communications, vol. 52, No. 8, pp. 1539-1554.
Schmidt et al., Apr. 2013, "Red-Light-Controlled Protein-RNA Crosslinking with a Genetically Encoded Furan", Angewandte Chemie International Edition, vol. 52, No. 17, pp. 4690-4693.
May 16, 2017, International Search Report and Written Opinion for International Patent Application No. PCT/EP2017/054708, 9 pages.
Sep. 13, 2018, International Preliminary Report on Patentability for International Patent Application No. PCT/EP2017/054708, 7 pages.

\* cited by examiner

*Primary Examiner* — Thomas S Heard
(74) *Attorney, Agent, or Firm* — Lathrop GPM LLP; James H. Velema, Esq.

(57) ABSTRACT

The present invention relates to a method for covalently binding a cell surface protein and a ligand, the ligand being capable of specifically binding to the cell surface protein, the method consisting essentially of contacting the living cells expressing the cell surface protein with the ligand comprising at least one furan moiety, thereby covalently binding the cell surface protein and the ligand.

11 Claims, 14 Drawing Sheets

1

2

4

6

MCF-7

MCF-7

HEK-myc-KISS1R

HEK-myc-KISS1R

"WTP"

H—Y-r-F-F—NH$_2$

Chemical Formula: $C_{33}H_{42}N_8O_5$
Exact Mass: 630,32782
Molecular Weight: 630,75000

"WTP-G"

H—Y-r-F-F-G—NH$_2$

Chemical Formula: $C_{35}H_{45}N_9O_6$
Exact Mass: 687,34928
Molecular Weight: 687,80200

"FUA3"

Chemical Formula: $C_{33}H_{43}N_9O_7$
Exact Mass: 677,32854
Molecular Weight: 677,76300

"FUA-G"

Chemical Formula: $C_{42}H_{52}N_{10}O_8$
Exact Mass: 824,39696
Molecular Weight: 824,94000

"FUA4"

Chemical Formula: $C_{33}H_{43}N_9O_7$
Exact Mass: 677,32854
Molecular Weight: 677,76300

METHODS FOR COVALENTLY BINDING A CELL SURFACE PROTEIN AND A LIGAND

RELATED APPLICATIONS

This application is a 35 U.S.C. § 371 filing of International Patent Application No. PCT/EP2017/054708, filed Mar. 1, 2017, which claims the benefit of priority to European Patent Application No. 16158059.2, filed Mar. 1, 2016. The entire contents of these applications are incorporated herein by reference for all purposes.

FIELD OF THE INVENTION

The present invention is broadly in the field of cell-based assays for detecting and/or identifying cell surface proteins or ligands specifically binding to cell surface proteins. In particular, the invention concerns a method for covalently binding a cell surface protein and a ligand. Further, the invention provides for cell-based assays.

BACKGROUND OF THE INVENTION

Interactions between ligands, such as peptides or small molecules, and cell surface proteins are crucial for numerous key processes in living organisms. Approximately one third of the mammalian genome encodes for membrane proteins. Activation and signalling of cell surface proteins are often involved in disease processes including malignant transformation. Identification of selective target membrane proteins can be used in the identification of biomarkers for early detection and prognosis of cancer but can also boost the discovery of new therapies. Moreover, mass spectrometry analysis has generated huge catalogues of possible bioactive peptides by the so-called peptidomics approaches. For many of these peptides that produce a biological effect it is currently not clear what their targets are or which molecular mechanisms they initiate. Indeed, for such orphan peptides the cell surface receptors or other protein partners generally remain unknown.

Today, the detection and visualisation of proteins, and more specifically cell surface proteins, is possible using a combination of primary and secondary antibodies. However, for the majority of cell surface proteins, no antibodies are commercially available and, even when available, the specificity (selectivity) and sensitivity (affinity) of commercially available polyclonal and monoclonal antibodies is often unsatisfactory for the detection of cell surface proteins. Furthermore, the use of antibodies is impossible for identifying unknown cell surface proteins.

Analysis of non-covalently bound cellular assemblies is, in particular for cell surface receptors, difficult for several reasons. Their hydrophobic nature and relatively low abundance precludes easy upscaling as they typically need to be in their natural environment to maintain binding properties. Activation of receptors by their ligands at the cell surface is based on the formation of a transient complex that, due to dynamic turnover, can be rapidly internalized and degraded. Immunoaffinity-based techniques for isolating ligand-receptor complexes from cell lysates are therefore rarely successful and can only be applied for high affinity interactions. Furthermore, interactomics techniques such as the yeast two-hybrid screen are unsuitable for the identification of extracellular protein-protein/peptide interactions. Elucidation of such interactions thus requires a technique compatible with living cells under physiological conditions.

In recent years, a whole range of bio-orthogonal chemistries was developed, allowing selective modification of biomolecules, in their natural environment. The introduced functional groups can react with a presented probe in an orthogonal way. Examples of such bio-orthogonal reactions include azide-alkyne cycloadditions, Staudinger ligation, and Diels Alder reactions. Despite the elegance and efficiency of these methods in labeling a wide variety of biomolecules, the need for modification of both binding partners with a specific unnatural reactive group represents a hurdle for general applicability.

Alternatively, photoaffinity crosslinking is based on the introduction of a photoreactive group which is able to form a crosslink with an unmodified natural binding partner upon activation with UV light. This requirement for an activation step limits the applicability of photo-crosslinking in complex biological settings such as living cells. Benzophenones, aryl azides and diazirines are among the most widely used groups. Although previously applied in the characterization of ligand-receptor complexes, these chemistries bear several disadvantages. Phototoxicity needs to be strictly monitored. Furthermore, the formation of highly reactive intermediates reduces selectivity of crosslinking. Therefore, experiments are generally carried out with cell lysates or, when working with living cells, in cold buffers. Benzophenones are typically bulky groups, which may negatively influence biological activity of the used probes. Aryl azides are much smaller, but the short-wave UV-light needed for their activation (<300 nm), is known to cause damage to the biological environment. Finally, diazirines are more stable, are excited at higher wavelengths, but their synthesis is quite tedious.

Recently, a crosslinking technology was developed based on a furan moiety. Furan represents a latent reactive moiety that needs primary oxidative activation to allow covalent bond formation with nucleophilic sites in its proximity. Furan, when incorporated in oligonucleotides, can be activated by oxidation using N-bromosuccinimide (NBS) (Halila et al., 2005, Chem. Commun. (Camb), 936-8) or singlet oxygen (Op de Beeck and Madder, 2012, J. Am. Chem. Soc., 134, 10737-40).

WO2012/085279 describes a method for crosslinking peptides comprising a furan moiety with second peptides. The method requires the addition of an activation signal to oxidize the furan moiety. The example section of WO2012/085279 illustrates that crosslinking furan-StrepTagII peptides with streptavidin required the addition of NBS as an activation signal to oxidize the furan moiety.

Although furan is commercially available, its use in cell-based assays has always been avoided in view of its toxicity and carcinogenicity. In the liver, cytochrome P450 catalyses oxidation of furan to a reactive aldehyde, which subsequently reacts with sulfhydryl and amine groups (Chen et al., 1997, Chem. Res. Toxicol., 10, 866-74).

In view of the above, there remains a need in the art to provide further and/or improved methods for detecting and/or identifying cell surface proteins or ligands specifically binding to cell surface proteins.

SUMMARY OF THE INVENTION

Prior art furan-based methods for crosslinking require an exogenous activation signal (such as N-bromosuccinimide or light) for oxidative activation of the furan moiety. Unexpectedly, the present inventors have found that the presence of such an activation signal is not necessary to obtain covalent binding between a cell surface protein and a ligand in living cells. The example section herein illustrates that a cell surface protein and a ligand, specifically binding to the cell surface protein, are covalently bound by contacting the living cells with the ligand comprising a furan moiety.

Hence, a first aspect of the present invention relates to a method for covalently binding a cell surface protein and a ligand, the ligand being capable of specifically binding to the cell surface protein, the method consisting essentially of contacting living cells expressing the cell surface protein with the ligand comprising at least one furan moiety, thereby covalently binding the cell surface protein and the ligand.

The methods illustrating the principles of the present invention advantageously allow covalently binding a cell surface protein and a ligand without the need for any exogenous (chemical or physical) activation. The present methods thus allow the formation of a covalent cell surface protein-ligand complex in situ under physiological conditions, e.g., using growth media. Advantageously, the present methods allow the covalent binding in diverse types of living cells such as but not limited to human cells, mouse cells, cancerous cells, and healthy cells. Furthermore, the present methods allow the covalent binding of a cell surface protein and a ligand without loss of efficiency or specificity compared to existing methods for crosslinking performed by the addition of an activation signal such as photoaffinity crosslinking. The observed efficiency, selectivity, and proximity-induced specific covalent binding of the present methods in combination with their compatibility with physiological conditions and zero cell toxicity make the methods illustrating the present invention superior to existing crosslinking techniques.

The present methods allow the identification of target cell surface proteins of biologically active orphan ligands, such as orphan peptides or small molecules, without the requirement for exogenous activation. For instance, the present methods allow to screen peptide libraries generated by standard solid phase peptide synthesis and to identify the cell surface protein, e.g. via mass spectrometry-based sequencing, if a covalently bound complex is present. Next to identifying the cell surface protein involved, the present methods allow to gain immediate insight on the location of the peptide binding site. Alternatively, the methods illustrating the present invention allow in situ receptor labeling, e.g. in diagnostics, as a cheap, reliable alternative to antibodies.

Hence, a further aspect relates to a cell-based assay for identifying, for a known ligand, a cell surface protein to which the ligand is capable of specifically binding thereto, the ligand comprising at least one furan moiety, the cell-based assay consisting essentially of:
  contacting living cells with the ligand;
  determining the presence of a covalently bound complex of the cell surface protein and the ligand; and
  identifying the cell surface protein if the covalently bound complex is present.

A further aspect relates to a cell-based assay for identifying, for a known cell surface protein, a ligand specifically binding to the cell surface protein, the cell-based assay consisting essentially of:
  contacting living cells expressing the cell surface protein with a ligand comprising at least one furan moiety;
  determining the presence of a covalently bound complex of the cell surface protein and the ligand;
  inferring from the finding that the covalently bound complex is present that the ligand specifically binds the cell surface protein.

Yet a further aspect relates to a cell-based assay for identifying a binding site of a cell surface protein and a peptide, the peptide being capable of specifically binding to the cell surface protein and the peptide comprising at least one amino acid comprising a furan moiety, wherein said amino acid comprising a furan moiety is located at position n of the peptide, the cell-based assay consisting essentially of:
(a) contacting living cells with the peptide;
(b) determining the presence of a covalently bound complex of the cell surface protein and the peptide;
(c) identifying the amino acid comprising a furan moiety as a binding site of the cell surface protein and the peptide if the covalently bound complex is present;
(d) optionally repeating steps (a) to (c) with peptides comprising a furan moiety, wherein the amino acid comprising a furan moiety is located at position n+p of the peptides comprising a furan moiety;
wherein position n may be any amino acid of the peptides comprising a furan moiety, and wherein p is a positive or negative integer (provided position n+p is located on the peptides comprising a furan moiety).

The ensuing statements provide additional illustration of certain aspects and embodiments that have been disclosed in accordance with the present invention:

1. A method for covalently binding a cell surface protein and a ligand, the ligand being capable of specifically binding to the cell surface protein, the method consisting essentially of contacting living cells expressing the cell surface protein with the ligand comprising at least one furan moiety, thereby covalently binding the cell surface protein and the ligand.

2. The method according to statement 1, wherein the cell surface protein is selected from the group consisting of a cell surface receptor, a cell adhesion molecule, and a cell surface protease.

3. The method according to statement 1 or 2, wherein the cell surface protein is a cell surface receptor selected from the group consisting of a G-protein coupled receptor (GPCR), an immune receptor, an ion channel-linked receptor, and an enzyme-linked receptor, preferably wherein the cell surface protein is a GPCR.

4. The method according to any one of statements 1 to 3, wherein the ligand is a peptide, a nucleoside, a nucleic acid, a lipid, a polysaccharide, a small molecule, or a combination thereof, preferably wherein the ligand is a peptide.

5. The method according to any one of statements 1 to 4, wherein the cell surface protein is a GPCR and the ligand is a peptide.

6. The method according to any one of statements 1 to 5, wherein the furan moiety of the ligand is oxidized by endogenous activation.

7. The method according to statement 6, wherein the endogenous activation occurs at the extracellular space of the cell membrane.

8. The method according to any one of statements 1 to 7, wherein the cell surface protein comprises at least one amine group, hydroxyl group, sulfhydryl group, imidazole group and/or indole group.

9. The method according to any one of statements 6 to 8, wherein the oxidized furan moiety of the ligand reacts with the amine group, hydroxyl group, sulfhydryl group, imidazole group and/or indole group of the cell surface protein.

10. The method according to any one of statements 1 to 9, wherein the method is performed under physiological conditions.

11. The method according to any one of statements 1 to 10, wherein the living cells are normal cells.

12. A method for detecting a cell surface protein covalently bound to a ligand, the ligand being capable of specifically binding to the cell surface protein, the method consisting essentially of:
    performing the method as defined in any one of statements 1 to 11, and
    detecting the cell surface protein covalently bound to the ligand, preferably by flow cytometry, microscopy, gel-electrophoresis, Western blot, immunoassays, mass spectrometry, or a combination thereof.
13. A cell-based assay for identifying, for a known ligand, a cell surface protein to which the ligand is capable of specifically binding thereto, the ligand comprising at least one furan moiety, the cell-based assay consisting essentially of:
    contacting living cells with the ligand;
    determining the presence of a covalently bound complex of the cell surface protein and the ligand; and
    identifying the cell surface protein if the covalently bound complex is present.
14. A cell-based assay for identifying, for a known cell surface protein, a ligand specifically binding to the cell surface protein, the cell-based assay consisting essentially of:
    contacting living cells expressing the cell surface protein with a ligand comprising at least one furan moiety;
    determining the presence of a covalently bound complex of the cell surface protein and the ligand; and
    inferring from the finding that the covalently bound complex is present that the ligand specifically binds the cell surface protein.
15. A cell-based assay for identifying a binding site of a cell surface protein and a peptide, the peptide being capable of specifically binding to the cell surface protein and the peptide comprising at least one amino acid comprising a furan moiety, wherein said amino acid comprising a furan moiety is located at position n of the peptide, the cell-based assay consisting essentially of:
    (a) contacting living cells with the peptide;
    (b) determining the presence of a covalently bound complex of the cell surface protein and the peptide;
    (c) identifying the amino acid comprising a furan moiety as a binding site of the cell surface protein and the peptide if the covalently bound complex is present;
    (d) optionally repeating steps (a) to (c) with peptides comprising a furan moiety, wherein the amino acid comprising a furan moiety is located at position n+p of the peptides comprising a furan moiety;
    wherein position n may be any amino acid of the peptides comprising a furan moiety, and wherein p is a positive or negative integer (provided position n+p is located on the peptides comprising a furan moiety).
16. The cell-based assay according to any one of statements 13 to 15, wherein
    the cell surface protein is selected from the group consisting of a cell surface receptor, a cell adhesion molecule, and a cell surface protease;
    the cell surface protein is a cell surface receptor selected from the group consisting of a G-protein coupled receptor (GPCR), an immune receptor, an ion channel-linked receptor, and an enzyme-linked receptor, preferably wherein the cell surface protein is a GPCR;
    the ligand is a peptide, a nucleoside, a nucleic acid, a lipid, a polysaccharide, a small molecule, or a combination thereof, preferably wherein the ligand is a peptide;
    the cell surface protein is a GPCR and the ligand is a peptide;
    the cell-based assay is performed under physiological conditions; and/or
    the living cells are normal cells.
17. A method for covalently binding a cell surface protein and a ligand, the ligand being capable of specifically binding to the cell surface protein, the method comprising or consisting essentially of contacting living cells expressing the cell surface protein with the ligand comprising at least one furan moiety without the addition of an exogenous activation signal, thereby covalently binding the cell surface protein and the ligand.
18. The method according to statement 17, wherein the cell surface protein is selected from the group consisting of a cell surface receptor, a cell adhesion molecule, and a cell surface protease.
19. The method according to statement 17 or 18, wherein the cell surface protein is a cell surface receptor selected from the group consisting of a G-protein coupled receptor (GPCR), an immune receptor, an ion channel-linked receptor, and an enzyme-linked receptor, preferably wherein the cell surface protein is a GPCR.
20. The method according to any one of statements 17 to 19, wherein the ligand is a peptide, a nucleoside, a nucleic acid, a lipid, a polysaccharide, a small molecule, or a combination thereof, preferably wherein the ligand is a peptide.
21. The method according to any one of statements 17 to 20, wherein the cell surface protein is a GPCR and the ligand is a peptide.
22. The method according to any one of statements 71 to 21, wherein the furan moiety of the ligand is oxidized by endogenous activation.
23. The method according to statement 22, wherein the endogenous activation occurs at the extracellular space of the cell membrane.
24. The method according to any one of statements 17 to 23, wherein the cell surface protein comprises at least one amine group, hydroxyl group, sulfhydryl group, imidazole group and/or indole group.
25. The method according to any one of statements 22 to 24, wherein the oxidized furan moiety of the ligand reacts with the amine group, hydroxyl group, sulfhydryl group, imidazole group and/or indole group of the cell surface protein.
26. The method according to any one of statements 17 to 25, wherein the method is performed under physiological conditions.
27. The method according to any one of statements 17 to 16, wherein the living cells are normal cells.
28. A method for detecting a cell surface protein covalently bound to a ligand, the ligand being capable of specifically binding to the cell surface protein, the method consisting essentially of:
    performing the method as defined in any one of statements 17 to 27, and
    detecting the cell surface protein covalently bound to the ligand, preferably by flow cytometry, microscopy, gel-electrophoresis, Western blot, immunoassays, mass spectrometry, or a combination thereof.
29. A cell-based assay for identifying, for a known ligand, a cell surface protein to which the ligand is capable of specifically binding thereto, the ligand comprising at least one furan moiety, the cell-based assay comprising or consisting essentially of:
    contacting living cells with the ligand without the addition of an exogenous activation signal;

determining the presence of a covalently bound complex of the cell surface protein and the ligand; and
identifying the cell surface protein if the covalently bound complex is present.
30. A cell-based assay for identifying, for a known cell surface protein, a ligand specifically binding to the cell surface protein, the cell-based assay comprising or consisting essentially of:
contacting living cells expressing the cell surface protein with a ligand comprising at least one furan moiety without the addition of an exogenous activation signal;
determining the presence of a covalently bound complex of the cell surface protein and the ligand; and
inferring from the finding that the covalently bound complex is present that the ligand specifically binds the cell surface protein.
31. A cell-based assay for identifying a binding site of a cell surface protein and a peptide, the peptide being capable of specifically binding to the cell surface protein and the peptide comprising at least one amino acid comprising a furan moiety, wherein said amino acid comprising a furan moiety is located at position n of the peptide, the cell-based assay comprising or consisting essentially of:
(a) contacting living cells with the peptide without the addition of an exogenous activation signal;
(b) determining the presence of a covalently bound complex of the cell surface protein and the peptide;
(c) identifying the amino acid comprising a furan moiety as a binding site of the cell surface protein and the peptide if the covalently bound complex is present;
(d) optionally repeating steps (a) to (c) with peptides comprising a furan moiety, wherein the amino acid comprising a furan moiety is located at position n+p of the peptides comprising a furan moiety;
wherein position n may be any amino acid of the peptides comprising a furan moiety, and wherein p is a positive or negative integer (provided position n+p is located on the peptides comprising a furan moiety).
32. The cell-based assay according to any one of statements 29 to 31, wherein
the cell surface protein is selected from the group consisting of a cell surface receptor, a cell adhesion molecule, and a cell surface protease;
the cell surface protein is a cell surface receptor selected from the group consisting of a G-protein coupled receptor (GPCR), an immune receptor, an ion channel-linked receptor, and an enzyme-linked receptor, preferably wherein the cell surface protein is a GPCR;
the ligand is a peptide, a nucleoside, a nucleic acid, a lipid, a polysaccharide, a small molecule, or a combination thereof, preferably wherein the ligand is a peptide;
the cell surface protein is a GPCR and the ligand is a peptide;
the cell-based assay is performed under physiological conditions; and/or
the living cells are normal cells.
In all of the above mentioned statements 1 to 16, the term "consisting essentially of" implies that no exogenous activation signal is added in the methods or cell-based assays. This means that in the methods or cell-based assays of any one of the above aspects, the covalent binding between the protein component and its ligand comprising a furan moiety is effectuated without the addition of an exogenous activation signal.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

BRIEF DESCRIPTION OF THE FIGURES

FIG. 6 represents photographs of a Western blot illustrating cell surface receptor-ligand crosslink formation on living cells using a comparative method for crosslinking (using NBS as an activation signal). Western blot of cell lysates prepared after crosslinking furan modified kisspeptin peptides on MDA-MB-231 cells.

FIG. 9 represents photographs of a Western blot illustrating covalent binding of a cell surface receptor and a ligand on living cells using a method according to embodiments of the present invention. The effect of the presence of a PEG-linker between the N-terminus and biotin-moiety of the ligand on the efficiency of covalent binding is shown.

FIG. 10 represents photographs of a Western blot illustrating covalent cell surface receptor-ligand complex formation on living cells using a method according to an embodiment of the present invention. Western blot of cell lysates prepared after covalently binding furan modified kisspeptin peptides on MDA-MB-231 cells in growth medium comprising 10% serum.

FIG. 11 represents photographs of a Western blot illustrating the covalent binding of furan modified kisspeptin and cell surface receptor GPR54 on NIH 3T3 cell line according to an embodiment of the present method. Western blot of cell lysates prepared after covalently binding furan-modified kisspeptin peptide 6.

FIG. 12 represents photographs of a Western blot illustrating the covalent binding of furan modified kisspeptin and cell surface receptor GPR54 on HeLa cell line according to an embodiment of the present method. Western blot of cell lysates prepared after covalently binding furan-modified kisspeptin peptide 6.

FIG. 13 represents photographs of a Western blot illustrating the covalent binding of furan modified kisspeptin and cell surface receptor GPR54 on MCF-7 cell line according to an embodiment of the present method. Western blot of cell lysates prepared after covalently binding furan-modified kisspeptin peptide 6.

FIG. 14 represents photographs of a Western blot illustrating the covalent binding of furan modified kisspeptin and cell surface receptor GPR54 on HEK-myc-KISS1R cell line according to an embodiment of the present method. Western blot of cell lysates prepared after covalently binding furan-modified kisspeptin peptide 6.

DETAILED DESCRIPTION OF THE INVENTION

Figure 1:
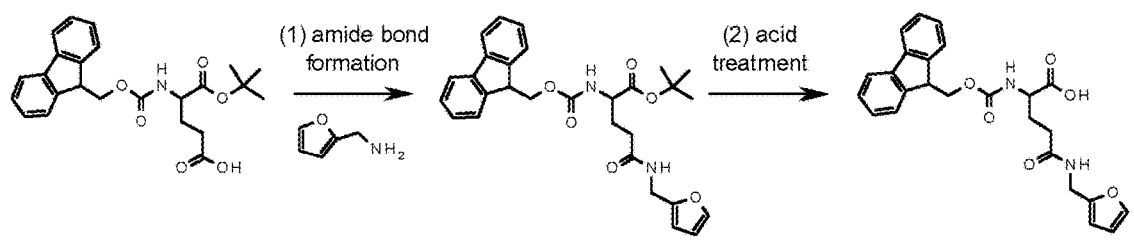
FIG. 1 represents a schematic overview illustrating the synthesis of a furan amino acid from a commercially available furyl amine derivative and a glutamic acid derivative. (1): amide bond formation; (2): acid treatment.

Before the present method and products of the invention are described, it is to be understood that this invention is not limited to particular methods, components, products or combinations described, as such methods, components, products and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The present inventors have found that the presence of an exogenous activation signal is not necessary to oxidize the furan moiety and obtain covalent binding of a cell surface protein and a ligand on living cells.

Hence, the present invention provides a method for covalently binding a cell surface protein and a ligand, the ligand being capable of specifically binding to the cell surface protein, the method consisting essentially of or consisting of contacting living cells expressing the cell surface protein with the ligand comprising at least one furan moiety, thereby covalently binding the cell surface protein and the ligand. The methods as taught herein are preferably performed in vitro.

The term "in vitro" generally denotes outside, or external to, animal or human body. The term "ex vivo" typically refers to tissues or cells removed from an animal or human body and maintained or propagated outside the body, e.g., in a culture vessel. The term "in vitro" as used herein should be understood to include "ex vivo". The term "in vivo" generally denotes inside, on, or internal to, animal or human body.

The present invention provides methods for covalently binding a cell surface protein as described herein and a ligand as described herein.

The terms "covalently binding", "covalent coupling", or "crosslinking" may be used interchangeably herein and refer to coupling a cell surface protein and a ligand with a covalent bond. The covalent bond renders the binding permanent as opposed to a transient binding.

The method advantageously allows site-selective coupling of a ligand to its cell surface receptor. The term "site-selective coupling", as opposed to non-selective or non-specific coupling, refers to the coupling of one or more determined monomers present or introduced in one or more determined positions of a ligand (e.g., one or more furan amino acids present or introduced in one or more determined positions of the furan-peptide) to a cell surface receptor.

Accordingly, in an embodiment, the invention relates to a method for the site-selective covalent binding of a cell surface protein and a ligand, the ligand being capable of specifically binding to the cell surface protein, the method consisting essentially of contacting the living cells expressing the cell surface protein with the ligand comprising at least one furan moiety.

Cell Surface Protein

The term "cell surface protein" as used herein refers to any protein present on the extracellular surface of a cell.

The terms "protein", "polypeptide", or "peptide" can be used interchangeably and relate to any natural or recombinant molecule comprising amino acids joined together by peptide bonds between adjacent amino acid residues. A "peptide bond", "peptide link" or "amide bond" is a covalent bond formed between two amino acids when the carboxyl group of one amino acid reacts with the amino group of the other amino acid, thereby releasing a molecule of water. The terms "amino acid" and "amino acid residue" may be used interchangeably herein.

The recitation "protein being present on the extracellular surface of a cell" encompasses that at least part of the protein is exposed to the extracellular space (or compartment) of the cell.

The "extracellular space of the cell" refers to the space (or compartment) at the extracellular or external side of the plasma membrane (i.e., cell membrane).

The number of amino acids of the cell surface protein is not limiting. In certain embodiments, the cell surface protein as taught herein may contain at least 20 amino acids. In certain embodiments, the cell surface protein as taught herein may contain from 20 to 20000 amino acids. In certain embodiments, the cell surface protein as taught herein may contain from 50 to 5000 amino acids, for example, the cell surface protein as taught herein may contain from 50 to 100 amino acids, or from 100 to 1000 amino acids, or from 1000 to 5000 amino acids. In certain embodiments, the cell surface protein as taught herein may contain from 5000 to 20000 amino acids, for example, the cell surface protein as taught herein may contain from 5000 to 10000 amino acids, or from 10000 to 20000 amino acids. For instance, the cell surface proteins as taught herein contain at least 20, at least 50, at least 100, at least 200, at least 300, at least 400, at least 500, at least 600, at least 700, at least 800, at least 900, at least 1000, at least 1500, at least 2000, at least 2500, at least 3000, at least 3500, at least 4000, or at least 4500 amino acids.

In certain embodiments, the cell surface protein may be an integral membrane protein, i.e., a protein which is permanently embedded in the cell membrane. Particularly, in certain embodiments, the cell surface protein may be an integral polytopic protein or transmembrane protein (i.e., an integral membrane protein that spans across the cell membrane at least once) or an integral monotopic protein (i.e., an integral membrane protein that is exposed on only one side (the extracellular side) of the cell membrane and does not span the whole way across the cell membrane).

In certain embodiments, the cell surface protein may be a peripheral membrane protein, i.e., a protein which is temporarily (and hence reversibly) attached either to the lipid bilayer of the cell membrane or to integral membrane proteins by a combination of hydrophobic, electrostatic, and other non-covalent interactions.

In certain embodiments, the cell surface protein may be a lipid-anchored protein (also known as lipid-linked protein), i.e., a protein which is covalently linked to a lipid, a glycolipid, or a glycosylphosphatidylinositol lipid that has its fatty acids inserted in the lipid bilayer of the cell membrane.

In certain embodiments, the cell surface protein may be modified, for instance by post-translational modification. For instance, the cell surface protein may be phosphorylated, tyrosine sulfated, and/or glycosylated. Post-translational modification of proteins can be experimentally detected by a variety of techniques, including mass spectrometry and Western blotting.

In certain embodiments, the cell surface protein may be an endogenous protein. This advantageously allows studying endogenous cell surface proteins, e.g., by visualizing the localization, internalization, trafficking and diffusion characteristics of endogenous cell surface proteins in the cell membrane.

The term "endogenous protein" refers to a protein resulting from expression of a nucleic acid, such as DNA, naturally found in the genome of the cell in which the protein is expressed.

By "nucleic acid" is meant oligomers and polymers of any length composed essentially of nucleotides, e.g., deoxyribonucleotides and/or ribonucleotides. Nucleic acids can comprise purine and/or pyrimidine bases and/or other natural (e.g., xanthine, inosine, hypoxanthine), chemically or biochemically modified (e.g., methylated), non-natural, or derivative nucleotide bases. The backbone of nucleic acids can comprise sugars and phosphate groups, as can typically be found in RNA or DNA, and/or one or more modified or substituted sugars and/or one or more modified or substituted phosphate groups. Modifications of phosphate groups or sugars may be introduced to improve stability, resistance to enzymatic degradation, or some other useful property. A "nucleic acid" can be for example double-stranded, partly double stranded, or single-stranded. Where single-stranded, the nucleic acid can be the sense strand or the antisense strand. In addition, nucleic acid can be circular or linear. The term "nucleic acid" as used herein preferably encompasses DNA and RNA, specifically including RNA, genomic RNA, cDNA, DNA, provirus, pre-mRNA and mRNA.

In certain embodiments, the cell surface protein may be an exogenous protein.

The term "exogenous protein" refers to a protein resulting from expression of a nucleic acid, such as DNA, not naturally found in the genome of but introduced into the cell in which the protein is expressed. The nucleic acid, such as DNA, can be transiently introduced in the cell in which the protein is expressed or can be stably introduced in the genome of the cell in which the protein is expressed. The nucleic acid, such as DNA, can be introduced in the cell in which the protein is expressed via methods known in the art such as transfection or viral infection (transduction). The nucleic acid, such as DNA, can be a derived from the genome of a different organism. The nucleic acid, such as DNA, can be wild type nucleic acid or recombinant nucleic acid.

In certain embodiments, the cell surface protein may be a wild-type protein. In certain embodiments, the cell surface protein may be a native protein.

As used herein, the term "wild-type" as applied to a nucleic acid or protein refers to a nucleic acid or a protein that occurs in, or is produced by, a biological organism as that biological organism exists in nature. The term "wild-type" may to some extent be synonymous with "native", the latter encompassing nucleic acids or proteins having a native sequence, i.e., ones of which the primary sequence is the same as that of the nucleic acids or proteins found in or derived from nature. A skilled person understands that native sequences may differ between or within different individuals of the same species due to normal genetic diversity (variation) within a given species. Also, native sequences may differ between or within different individuals of the same species due to post-transcriptional or post-translational modifications. Any such variants or isoforms of nucleic acids or polypeptides are encompassed herein as being "native". Accordingly, all sequences of nucleic acids or proteins found in or derived from nature are considered "native".

In certain embodiments, the cell surface protein may be a recombinant protein.

The term "recombinant" is generally used to indicate that the material (e.g., a nucleic acid, a genetic construct or a protein) has been altered by technical means (i.e., non-naturally) through human intervention. The term "recombinant nucleic acid" commonly refers to nucleic acids comprised of segments joined together using recombinant DNA technology. The term may denote material (e.g., a nucleic acid, a genetic construct or a protein) that has been altered by technical means of mutagenesis. As used herein the term "recombinant protein" refers to a protein that can result from the expression of recombinant nucleic acid such as recombinant DNA.

In certain embodiments of the methods or cell-based assays as taught herein, the cell surface protein may be selected from the group consisting of a cell surface receptor, a cell adhesion molecule, and a cell surface protease.

The terms "cell surface receptor", "membrane receptor", or "transmembrane receptor" can be used interchangeably herein and refer to a receptor present on the extracellular surface of a cell.

The term "receptor" generally refers to a protein that is capable of acting in cell signaling by receiving (specifically binding to) an extracellular agent (referred to herein as the "ligand").

The term "cell-adhesion molecule (CAM)" refers to a protein located on the surface of a cell and involved in binding with other cells or with the extracellular matrix (ECM), i.e., involved in cell adhesion.

CAMs are typically transmembrane receptors composed of three parts: an intracellular domain that interacts with the cytoskeleton, a transmembrane domain, and an extracellular domain that interacts either with other CAMs of the same kind (homophilic binding) or with other CAMs or the extracellular matrix (heterophilic binding).

In certain embodiments, the CAM is a calcium-independent CAM. In certain embodiments, the CAM is a calcium-independent CAM selected from an immunoglobulin superfamily CAM (IgSF CAM) or a lymphocyte homing receptor. Examples of lymphocyte homing receptors or addressins are CD34 and GLYCAM-1.

In certain embodiments, the CAM is a calcium-dependent CAM. In certain embodiments, the CAM is a calcium-dependent CAM selected from the group consisting of integrins, cadherins, and selectins.

In certain embodiments, the CAM is a cell-surface receptor.

The term "cell surface protease" or "membrane anchored protease" refers to a protein located on the surface of a cell and comprising a protease domain.

Non-limiting examples of membrane anchored proteases are A Disintegrin And Metalloproteinase domain-containing proteins (ADAM) or sheddase, and membrane-type matrix metalloproteinases (MT-MMPs).

In certain embodiments of the methods or cell-based assays as taught herein, the cell surface protein may be a cell surface receptor selected from the group consisting of a G-protein coupled receptor (GPCR), an immune receptor, an ion channel-linked receptor, and an enzyme-linked receptor.

In certain embodiments of the methods or cell-based assays as taught herein, the cell surface protein may be a GPCR.

The terms "G protein-coupled receptor (GPCR)", "seven-transmembrane domain receptor", "7TM receptor", "hepta-helical receptor", "serpentine receptor", or "G protein-linked receptor (GPLR)" refer to receptors that possess seven transmembrane helices.

Upon ligand binding, GPCRs activate a G protein located on the intracellular side. G proteins are trimeric proteins. The 3 subunits of a G protein are called α, β, and γ. When a ligand binds to the GPCR it causes a conformational change in the GPCR, which allows it to act as a guanine nucleotide exchange factor. The GPCR can then activate an associated G protein by exchanging its bound GDP for a GTP. The G protein's a subunit, together with the bound GTP, can then dissociate from the β and γ subunits to further affect intracellular signaling proteins or target functional proteins directly depending on the a subunit type.

G protein-coupled receptors are found only in eukaryotes including yeast and animals.

Although numerous classification schemes have been proposed, the superfamily was classically divided into three main classes (A, B and C) with no detectable shared sequence homology between classes. More recently, an alternative classification system called GRAFS (Glutamate, Rhodopsin, Adhesion, Frizzled/Taste2, Secretin) has been proposed. By this system, GPCRs can be grouped into 6 classes based on sequence similarity (homology) and functional similarity: Class A (or 1) (Rhodopsin-like); Class B (or 2) (Secretin receptor family); Class C (or 3) (Metabotropic glutamate/pheromone); Class D (or 4) (Fungal mating pheromone receptors); Class E (or 5) (Cyclic AMP receptors); or Class F (or 6) (Frizzled/Smoothened).

In certain embodiments of the methods or cell-based assays as taught herein, the GPCR may be KiSS1-derived peptide receptor (GPR54), C—X—C chemokine receptor type 4 (CXCR4), or C—C chemokine receptor type 5 (CCR5).

In certain embodiments, the cell surface protein may be GPR54 and the ligand may be kisspeptin-10 peptide.

GPR54 (also known as Kisspeptin receptor) is a G protein-coupled receptor which binds the peptide hormone kisspeptin (metastin).

In certain embodiments, the cell surface protein may be CXCR4 and the ligand may be CVX15.

CXCR4 (also known as CXCR-4 or fusin or CD184) is an alpha-chemokine receptor for stromal-derived-factor-1 (SDF-1, also called CXCL12). CVX15 is a peptide antagonist of the G-protein coupled receptor CXCR4.

In certain embodiments, the cell surface protein may be CCR5 and the ligand may be Maraviroc.

CCR5 (also known as CD195) is a protein on the surface of white blood cells that is involved in the immune system as it acts as a receptor for chemokines. Maraviroc is a small molecule antagonist of CCR5.

In certain embodiments of the methods or cell-based assays as taught herein, the cell surface protein may be an immune receptor.

The terms "immune receptor" and "immunologic receptor" as used herein refer to a cell surface receptor which binds to an extracellular agent (for example, a cytokine) and causes a response in the immune system.

In certain embodiments, the immune receptors may be pattern recognition receptors (PRRs) such as Toll-like receptors (TLRs) or NOD-like receptors (NLRs); killer activated receptors (KARs); killer inhibitor receptors (KIRs); complement receptors; Fc receptors; B cell receptors; T cell receptors; or cytokine receptors.

In certain embodiments of the methods or cell-based assays as taught herein, the cell surface protein may be an ion channel-linked receptor.

The terms "ion channel-linked receptors" or "ligand-gated ion channels (LGICs)" refer to receptors comprising a transmembrane domain including an ion pore, and an extracellular domain including a ligand binding location (an allosteric binding site). Ion channel-linked receptors allow ions (such as $Na^+$, $K^+$, $Ca^{2+}$, or $Cl^-$) to pass through the cell membrane in response to the binding of a ligand such as a neurotransmitter.

The ion channel-linked receptors constitute a large family of multi-pass transmembrane proteins. LGICs are classified into three families which lack evolutionary relationship: Cys-loop receptors, Ionotropic glutamate receptors and ATP-gated channels.

In certain embodiments of the methods or cell-based assays as taught herein, the cell surface protein may be an enzyme-linked receptor.

The terms "enzyme-linked receptors" or "catalytic receptors" refer to receptors comprising an extracellular ligand-binding domain, a transmembrane helix, and an intracellular catalytic domain.

Typically, the binding of an extracellular agent to an enzyme-linked receptor causes direct or indirect enzymatic activity on the intracellular side.

Enzyme-linked receptors are typically single-pass transmembrane receptors, with the enzymatic component of the receptor kept intracellular. There are six known types of enzyme-linked receptors: Receptor tyrosine kinases; Tyrosine kinase associated receptors; Receptor-like tyrosine phosphatases; Receptor serine/threonine kinases; Receptor Guanylyl cyclases; and Histidine kinase associated receptors.

Ligand

The term "ligand" refers to any agent capable of comprising at least one furan moiety. The nature of the ligand is not limited as long as the ligand is capable of comprising at least one furan moiety. In certain embodiments, the ligand may be a natural ligand such as a neurotransmitter (e.g., serotonin, dopamine, gamma-aminobutyric acid (GABA), or glutamate). In certain embodiments, the ligand may be a synthetic or artificial ligand such as a drug.

The term "furan moiety", "furan", "furyl" or "furyl-moiety" as used herein relates to a heterocyclic organic compound or functional group consisting of a five-membered aromatic ring with four carbon atoms and one oxygen atom.

In certain embodiments, the furan moiety may be bound to the ligand with one or two carbon atoms of the furan moiety. In certain embodiments, the furan moiety may be bound to the ligand with two carbon atoms of the furan moiety. For instance, the furan moiety may be bound to the ligand with the carbon atoms at position 2 and 3, or with the carbon atoms at position 2 and 4, or with the carbon atoms at position 2 and 5, or with the carbon atoms at position 3 and 4 of the furan moiety.

In certain preferred embodiments, the furan moiety may be bound to the ligand with one carbon atom of the furan moiety. In certain preferred embodiments, the furan moiety may be bound to the ligand with one carbon atom at position 2 of the furan moiety. In certain preferred embodiments, the furan moiety may be bound to the ligand with one carbon atom at position 3 of the furan moiety. Hence, in certain embodiments, the ligand may be a ligand comprising at least one furan moiety of Formula Ia or Formula Ib. In certain embodiments, the ligand may be a ligand comprising at least one furan moiety of Formula Ia. Such ligands advantageously allow efficient crosslinking of the ligand with the cell surface protein.

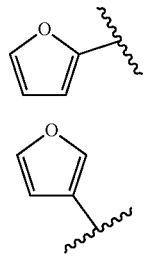

In certain embodiments, the ligands as taught herein may comprise at least one furan moiety. In certain embodiments, the ligands as taught herein may comprise more than one, such as, for instance, 2, 3, 4, 5, 6, 7, 8, 9, or 10 furan moieties. In certain embodiments, the ligands may comprise only one furan moiety. The furan moieties as taught herein can be located on any position in the ligand.

In certain embodiments, the ligands as taught herein may be provided in solution. The ligands as taught herein may be provided in a solvent wherein the ligands can be dissolved. In certain embodiments, the solvent is a polar protic solvent (such as water, methanol, or ethanol), a polar aprotic solvent (such as DMSO, dimethylformamide (DMF), acetonitrile, or tetrahydrofuran (THF)), or a non-polar solvent (such as chloroform or dichloromethane (DCM)). In certain embodiments, the ligands as taught herein may be provided in a solvent comprising or consisting of a polar protic solvent (such as water, methanol, or ethanol), a polar aprotic solvent (such as DMSO, DMF, acetonitrile, or THF), or an apolar solvent (such as chloroform or DCM).

In certain embodiments, the ligand may be capable of specifically binding to the cell surface protein.

The terms "specifically binding" or "specific binding" as used herein refer to the ability of a ligand to preferentially bind to a particular cell surface protein that is present alongside different cell surface proteins. In certain embodiments, a specific binding interaction will discriminate between desirable (target) and undesirable (non-target) cell surface proteins, in some embodiments more than about 10-fold, more than about 100-fold (e.g., more than about 1000- or 10,000-fold).

Accordingly, a ligand as taught herein is said to "specifically bind to" a particular cell surface protein when that ligand has affinity for, specificity for and/or is specifically directed to that cell surface protein (or to at least one part or fragment thereof). The dissociation constant ($K_d$) of the ligand as taught herein and the cell surface protein as taught herein relates to the affinity between the ligand and the cell surface protein.

The "specificity" of a ligand can be determined based on affinity for the cell surface protein. In certain embodiments, a ligand is capable of specifically binding to a cell surface protein when the dissociation constant of the ligand and the cell surface protein is at most 10 μM (i.e., $10^{-5}$ M). For instance, a ligand may be capable of specifically binding to a cell surface protein when the dissociation constant of the ligand and the cell surface protein is at most 1 μM (i.e., $10^{-6}$ M or $10^3$ nM), at most $10^2$ nM, at most 10 nM, at most 1 nM, at most 0.1 nM, at most 0.01 nM, at most 1 pM, or at most 1 fM. Preferably, a ligand is capable of specifically binding to a cell surface protein when the dissociation constant of the ligand and the cell surface protein is at most 1 nM (i.e., $10^{-9}$ M), more preferably at most 1 pM (i.e., $10^{-12}$ M).

A ligand as taught herein is said to be "specific for a first cell surface protein as opposed to a second cell surface protein" when it binds to the first cell surface protein with an affinity that is at least 5 times, such as at least 10 times, such as at least 100 times, and preferably at least 1000 times higher than the affinity with which that ligand as taught herein binds to the second cell surface protein. Accordingly, in certain embodiments, when a ligand as taught herein is said to be "specific for" a first cell surface protein as opposed to a second cell surface protein, it may specifically bind to (as defined herein) the first cell surface protein but not to the second cell surface protein.

In certain embodiments, the ligand as taught herein may comprise a label.

The term "label" as used herein refers to any atom, molecule, moiety or biomolecule that can be used to provide a detectable and preferably quantifiable read-out or property, and that can be attached to or made part of an entity of interest, such as the ligand as taught herein. Labels may be suitably detectable by mass spectrometric, spectroscopic, optical, colorimetric, magnetic, photochemical, biochemical, immunochemical or chemical means. Labels include without limitation dyes; radiolabels such as $^{32}$P, $^{33}$P, $^{35}$S, $^{125}$I, $^{131}$I; electron-dense reagents; enzymes (e.g., horseradish peroxidase (HRP) or alkaline phosphatase as commonly used in immunoassays); binding moieties such as biotin-streptavidin; haptens such as digoxigenin; nanoparticles such as gold nanoparticles or quantum dots; luminogenic, phosphorescent or fluorogenic moieties; mass tags; and fluorescent agents, alone or in combination with moieties that can suppress or shift emission spectra by fluorescence resonance energy transfer (FRET).

In certain embodiments, the ligand as taught herein may comprise a fluorophore, a non-fluorescent label, or a combination thereof.

In certain embodiments, the ligand as taught herein may comprise a fluorophore. The fluorophore may advantageously serve as a marker (or dye, or tag, or reporter) for the cell surface protein to which the ligand is bound. The fluorophore may allow to detect the cell surface protein to which the ligand is bound in a variety of analytical methods as defined herein such as fluorescent imaging, spectroscopy, and fluorescence-activated cell sorting (FACS).

The term "fluorophore", "fluorescent agent", or "fluorescent probe" generally refers to a chemical compound that can re-emit light upon light excitation.

In certain embodiments, the fluorophore may comprise a moiety excitable by near infrared (NIR) light such as borondipyrromethene (BODIPY), rhodamine, cyanine, phthalocyanines, and squaraine. In certain embodiments, the fluorophore may comprise a fluorescein moiety, a rhodamine moiety, a coumarin moiety, a cyanine moiety, BODIPY moiety, phthalocyanine moiety, or squaraine moiety.

In certain embodiments, the fluorophore may comprise or consist of fluorescent nanoparticles such as quantum dots or nanocrystals.

Suitable non-limiting examples of commercially available fluorophores are Alexa Fluor® Dyes (Thermo Fischer Scientific Inc., Massachusetts, USA), DyLight® Fluors (Thermo Fischer Scientific Inc., Massachusetts, USA), BODIPY Dyes (Thermo Fischer Scientific Inc., Massachusetts, USA), VivoTag Fluorochromes (PerkinElmer, Mass., USA), XenoLight CF™ fluorescent labeling dyes (PerkinElmer, Mass., USA), Atto Dyes (Sigma-Aldrich, MO, USA), and Tracy Dyes (Sigma-Aldrich, MO, USA).

In certain embodiments, the ligand as taught herein may comprise a non-fluorescent label including but not limited to dyes; radiolabels such as $^{32}P$, $^{33}P$, $^{35}S$, $^{125}I$, $^{131}I$; electron-dense reagents; enzymes (e.g., horse-radish peroxidase (HRP) or alkaline phosphatase as commonly used in immunoassays); biotin-streptavidin; haptens such as digoxigenin; and mass tags. The non-fluorescent label such as biotin may allow conjugation, isolation, and purification of the cell surface protein to which the ligand is bound.

The label may be coupled to the ligand by methods known in the art. For instance, the label may be coupled to the ligand by N-terminal modification during solid phase peptide synthesis (SPPS). Alternatively, introduction of an orthogonally protected Lysine derivative can be followed by selective deprotection and labeling. Also, a site-specifically incorporated and unique cysteine residue can be modified using fluorescent maleimides. Introduction of orthogonal functionalities, such as azide, alkyne and alkene, can be followed by labeling through click chemistry approaches, such as azide/alkyne, tetrazine/alkene, and thiol/ene.

For example, the label may be a mass-altering label. Preferably, a mass-altering label may involve the presence of a distinct stable isotope in one or more amino acids of a peptide vis-à-vis its corresponding non-labelled peptide. Mass-labelled peptides are particularly useful as positive controls, standards and calibrators in mass spectrometry applications. In particular, peptides including one or more distinct isotopes are chemically alike, separate chromatographically and electrophoretically in the same manner and also ionise and fragment in the same way. However, in a suitable mass analyser such peptides and optionally select fragmentation ions thereof will display distinguishable m/z ratios and can thus be discriminated. Examples of pairs of distinguishable stable isotopes include H and D, $^{12}C$ and $^{13}C$, $^{14}N$ and $^{15}N$ or $^{16}O$ and $^{18}O$. Usually, peptides and proteins of biological samples may substantially only contain common isotopes having high prevalence in nature, such as for example H, $^{12}C$, $^{14}N$ and $^{16}O$. In such case, the mass-labelled peptide may be labelled with one or more uncommon isotopes having low prevalence in nature, such as for instance D, $^{13}C$, $^{15}N$ and/or $^{18}O$. It is also conceivable that in cases where the peptides or proteins of a biological sample would include one or more uncommon isotopes, the mass-labelled peptide may comprise the respective common isotope(s).

Isotopically-labelled synthetic peptides may be obtained inter alia by synthesis or recombinant production of such peptides using one or more isotopically-labelled amino acid substrates, or by chemically or enzymatically modifying unlabelled peptides to introduce thereto one or more distinct isotopes. By means of example and not limitation, D-labelled peptides may be synthesised or produced by recombinant production in the presence of commercially available deuterated L-methionine $CH_3$—S—$CD_2CD_2$—CH(NH$_2$)—COOH or deuterated arginine $H_2NC(=NH)$—NH—$(CD_2)_3$—CD(NH$_2$)—COOH. It shall be appreciated that any amino acid of which deuterated or $^{15}N$- or $^{13}C$-containing forms exist may be considered for synthesis or recombinant production of labelled peptides. In another non-limiting example, a peptide may be treated with trypsin in $H_2^{16}O$ or $H_2^{18}O$, leading to incorporation of two oxygens ($^{16}O$ or $^{18}O$, respectively) at the COOH-termini of said peptide (e.g., US 2006/105415).

In certain embodiments of the methods or cell-based assays as taught herein, the ligand may be a peptide, a nucleoside, a nucleic acid, a lipid, a polysaccharide, a small molecule, or a combination thereof.

In certain embodiments of the methods or cell-based assays as taught herein, the ligand as taught herein may be a peptide.

Accordingly, in certain embodiments, the present invention relates to a method for covalently binding a cell surface protein and a peptide, the peptide being capable of specifically binding to the cell surface protein, the method consisting essentially of contacting living cells expressing the cell surface protein with the peptide comprising at least one furan moiety, thereby covalently binding the cell surface protein and the peptide.

The term "furan-peptide" as used herein refers to any peptide comprising a furan moiety. The methods or cell-based assays as taught herein may make use of furan-peptides.

In certain embodiments, the furan-peptide is a peptide comprising a furan moiety of Formula Ia.

The furan-peptides as taught herein comprise at least one furan moiety. The furan-peptides may comprise more than one, such as, for instance, 2, 3, 4, 5, 6, 7, 8, 9, 10, 11, 12, 13, 14, 15, 16, 17, 18, 19 or 20 furan moieties. In certain embodiments, the furan-peptide may comprise only one furan moiety. The furan moieties as taught herein can be located at any position in the furan-peptide, such as, for instance, N-terminally, C-terminally or internally. For instance, in case of more than one furan moiety, a first furan moiety may be located C-terminally and a further furan moiety may be located internally and/or N-terminally in a furan-peptide.

The furan-peptides as taught herein can be obtained by any suitable method known by the person skilled in the art.

In certain embodiments, the furan-peptides as taught herein can be obtained by incorporating at least one furan moiety during solid-phase peptide synthesis (SPPS) of a peptide. Solid-phase peptide synthesis is a method that is widely used to chemically synthesize peptides (see, e.g., Merrifield, 1963, *JACS*, 85, 2149-2154) and can be adapted to produce furan-peptides. This technique typically comprises two stages: the first stage of solid phase peptide synthesis (SPPS) includes the assembly of a peptide chain using protected amino acid derivatives on a solid support via repeated cycles of coupling-deprotection. The free N-terminal amine of a solid-phase attached peptide can then be coupled to the C-terminal carboxyl of a single N-protected amino acid unit, e.g., a furan amino acid. This unit is then deprotected, revealing a new N-terminal amine to which a further amino acid may possibly be attached. While the peptide is being synthesized usually by stepwise methods, all soluble reagents can be removed from the peptide-solid support matrix by filtration and washed away at the end of each coupling step. In the second stage of SPPS, the peptide is cleaved from the support and side-chain protecting groups are removed to produce the peptide, e.g., a furan-peptide.

There are two major used forms of solid phase peptide synthesis: Fmoc (Carpino et al., 1972, *J. Org. Chem.*, 37, 3404-3409), in which a base labile alpha-amino protecting group is used, and t-Boc, in which an acid labile protecting group is used. Each method involves different solid support resins and amino acid side chain protection and consequent cleavage/deprotection steps. For additional details regarding peptide synthesis, see the following publications and references cited within: Crick et al., 1961, *Nature*, 192, 1227-32; Hofmann et al., 1966, *JACS*, 88, 5914-9; Kaiser et al., 1989, *Acc. Chem. Res.*, 22, 47-54; Nakatsuka et al., 1987, *JACS*, 109, 3808-10; Schnolzer et al., 1992, *Science*, 5054, 221-5;

Chaiken et al., 1981, *CRC Crit. Rev. Biochem.*, 11, 255-301; Offord, 1987, *Protein Eng*, 1, 151-157; and Jackson et al., 1994, *Science*, 5183: 243-7; all of which are incorporated herein explicitly by reference.

In certain embodiments, the furan-peptides as taught herein can be obtained by incorporating at least one furan amino acid into a peptide during protein translation in prokaryotes such as bacteria, e.g. *E. coli*, or in eukaryotes such as yeast or mammalian cells, as described by Young and Schultz (2010, *J. Biol. Chem.*, 285(15), 11039-44).

The genetic encoding of a furan amino acid in *Escherichia coli* and in human cells has been described by Schmidt et al. (Schmidt et al., 2013, Angew. Chem. Int. Ed., 52, 4690-4693; Schmidt et al., 2013, Angew. Chem., 125, 4788-4791; Schmidt et al., 2014, Chem Bio Chem., 15(12):1755-60).

The furan amino acid as taught herein can be any amino acid comprising a furan moiety, for example, the furan amino acid as taught herein may be selected from a furyl-glycine, furyl-alanine, furyl-valine, furyl-leucine, furyl-isoleucine, furyl-proline, furyl-tyrosine, furyl-tryptophan, furyl-phenylalanine, furyl-cysteine, furyl-methionine, furyl-serine, furyl-threonine, furyl-lysine, furyl-arginine, furyl-histidine, furyl-aspartic acid, furyl-glutamic acid, furyl-asparagine or furyl-glutamine. In certain embodiments, the furan amino acid as taught herein may be furyl-alanine, furyl-glycine, or furyl-phenylalanine. Preferably, the furan amino acid as taught herein may be furylalanine, for example furyl-L-alanine or furyl-D-alanine, more preferably furyl-L-alanine. An important advantage of furyl-alanine is that it is commercially available. Moreover, furyl-alanine can be considered isosteric with histidine and iso-electronic with histidine and tyrosine. Consequently, no or minimal destabilization or alteration of the native protein structure is expected when incorporating furylalanine in a peptide.

The furan amino acid as taught herein can be an Fmoc-protected or tBoc-protected furan amino acid which allows easy incorporation into peptides through solid-phase peptide synthesis. For example, Fmoc-protected furyl-alanine, which provides the required handle for subsequent orthogonal labeling, is a commercially available amino acid.

The furan amino acid as taught herein may further be a furan amino acid as described by Schmidt et al. (2014, Chem Bio Chem., 15(12), 1755-60).

The furan amino acid as taught herein may further be obtained through standard organic synthesis using commercially available furan derivatives and commercially available amino acid derivatives. Commercially available furan derivatives used in the methods as described herein comprise both 2- and 3-substituted furan derivatives. For instance, commercially available furan derivatives can be selected from, but are not limited to compounds of Formula (IIIa), (IIIb), (IIIc), (IIId), (IIIe), (IIIf) or (IIIg), (IIIh), (IIIi), (IIIj), (IIIk) or stereoisomeric forms thereof.

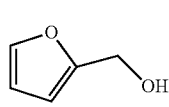

(IIIa)

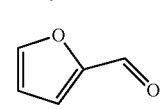

(IIIb)

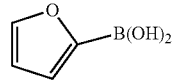

(IIIc)

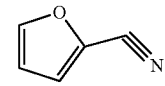

(IIId)

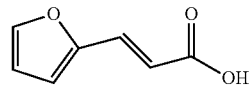

(IIIe)

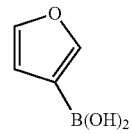

(IIIf)

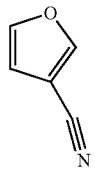

(IIIg)

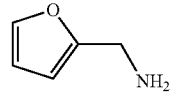

(IIIh)

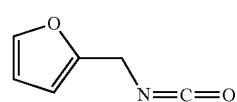

(IIIi)

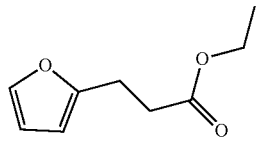

(IIIj)

(IIIk)

Starting from commercially available furan derivatives, other furan derivatives are within reach through standard organic synthesis known to the skilled person.

Commercially available amino acid derivatives used in the methods as described herein can for example be selected from but are not limited to compounds with Formula (IVa) or (IVb), or stereoisomeric forms thereof,

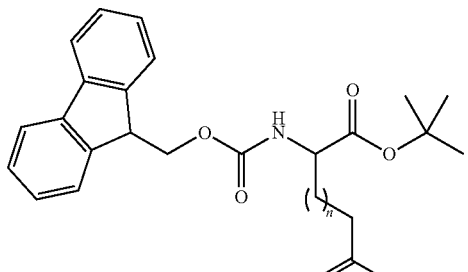

(IVa)

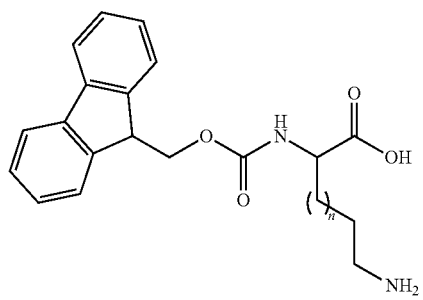

(IVb)

wherein n is an integer selected from 0, 1 or 2.

Figure 2:
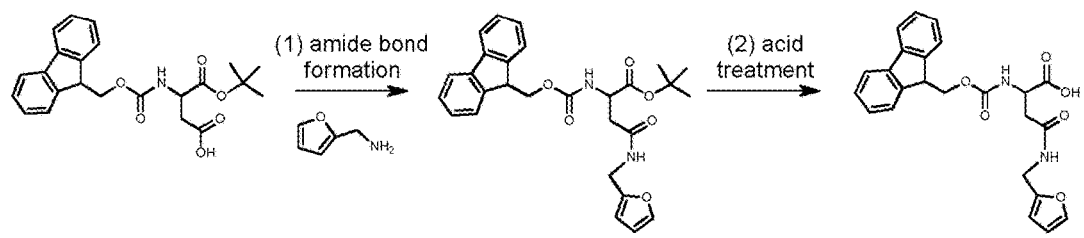
FIG. 2 represents a schematic overview illustrating the synthesis of a furan amino acid from a commercially available furyl amine derivative and an aspartic acid derivative. (1): amide bond formation; (2): acid treatment.
Figure 3A:
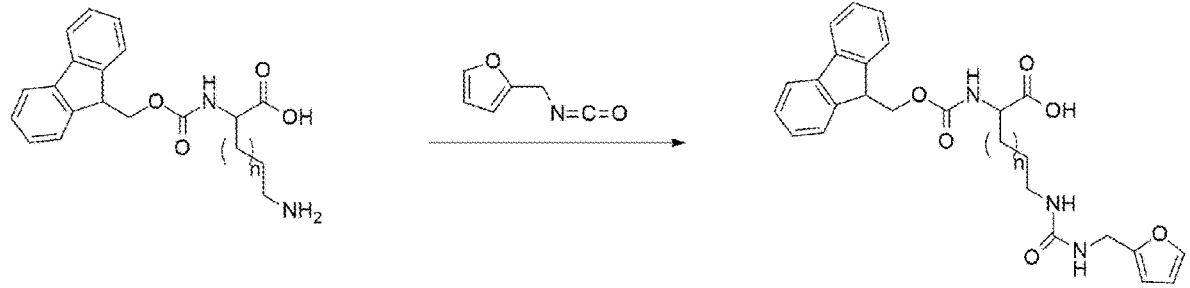
FIG. 3A and FIG. 3B represent a schematic overview illustrating the synthesis of a furan amino acid from a lysine derivative and a commercially available furyl isocyanate derivative or a furyl carboxylic acid derivative, respectively.
Figure 3B:
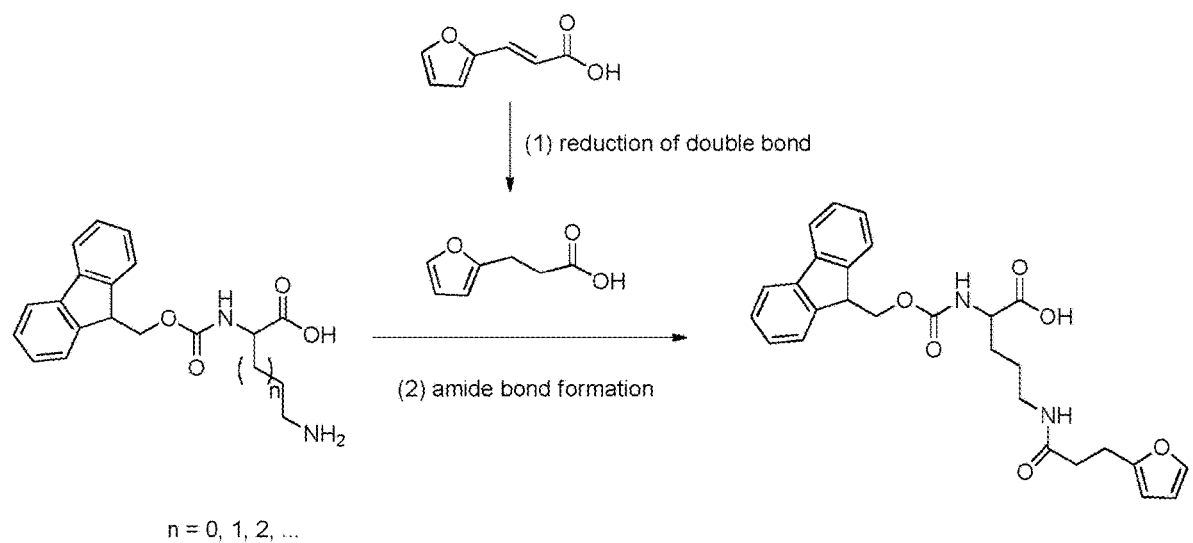

In an embodiment, the furan amino acids as taught herein are obtained through amide bond formation between a furyl amine derivative and the carboxyl group of a glutamic acid (Glu) derivative as depicted in FIG. 1. Furthermore, in an embodiment, the furan amino acids as taught herein may be obtained through amide bond formation between a furyl amine derivative and the carboxyl group of an aspartic acid (Asp) derivative as shown in FIG. 2. In an embodiment, the furan amino acids as taught herein may further be obtained through amide bond formation between a furyl isocyanate derivative or a furyl carboxylic acid derivative and the amine group of Lys as shown in FIG. 3A and FIG. 3B, respectively.

In certain embodiments, the furan amino acid as taught herein can be located in any position in the peptide. It will be understood by the skilled person, however, that sterical hindrance, e.g. of the furan amino acid, by other amino acids of the peptide should preferably be avoided. The furan amino acid as taught herein is preferably located in a position in the furan-peptide being accessible for binding to the cell surface protein. The position of the furan amino acid or furan moiety as taught herein in the peptide is preferably chosen based on, e.g., whether its position in a particular location would change the conformation, activity or stability of the peptide.

In an embodiment, the furan-peptides as taught herein may contain at least two amino acids. Preferably, the furan-peptides as taught herein may contain from 3 to 5000 amino acids. For example, the furan-peptides as taught herein may contain from 3 to 30 amino acids, for example, the furan-peptides as taught herein may contain from 3 to 10, or from 10 to 20, or from 20 to 30 amino acids. In certain embodiments, the furan-peptides as taught herein may contain from 20 to 50 amino acids, or from 50 to 100 amino acids, or from 100 to 1000, or from 1000 to 5000 amino acids. For example, the furan-peptides as taught herein may contain at least 20, at least 25, at least 30, at least 35, at least 40, at least 45, at least 50, at least 60, at least 70, at least 80, at least 90, at least 100, at least 200, at least 300, at least 400, at least 500, at least 600, at least 700, at least 800, at least 900 or at least 1000 amino acids.

In certain embodiments, the furan-peptides as taught herein may be unbound furan-peptides or furan-peptides bound to a solid support. In preferred embodiments, the furan-peptide as taught herein may be an unbound furan-peptide.

The terms "free", "deprotected", or "unbound" denote that the peptide is not coupled to a solid support (e.g. the furan-peptide is cleaved from the solid support) on which it is synthesized or the furan-peptide is produced by protein translation. The free or unbound furan-peptides as taught herein include, but are not limited to, furan-peptides in solution and dried or lyophilized furan-peptides, such as, for instance a powder of furan-peptides.

The furan-peptides as taught herein may be provided in dried or lyophilized form, such as, for instance a powder of furan-peptides.

The furan-peptides as taught herein may be provided in solution. The furan-peptides as taught herein may be provided in a solvent wherein the furan-peptides can be dissolved. In certain embodiments, the solvent is a polar protic solvent (such as water, methanol, or ethanol), a polar aprotic solvent (such as DMSO, dimethylformamide (DMF), acetonitrile, or tetrahydrofuran (THF)), or a non-polar solvent (such as chloroform or dichloromethane (DCM)). In certain embodiments, the furan-peptides as taught herein are provided in a solvent comprising or consisting of a polar protic solvent (such as water, methanol, or ethanol), a polar aprotic solvent (such as DMSO, DMF, acetonitrile, or THF), or an apolar solvent (such as chloroform or DCM).

The solid support for peptide synthesis is any support on which the furan-peptides as taught herein are synthesized. The solid supports for peptide synthesis may be polystyrene resins comprising an acid labile linker, a base-labile linker, or a photo-labile linker, or any other linker known in the art. The solid supports for peptide synthesis may also be polyethylene glycol (PEG) resins comprising an acid labile linker, a base-labile linker, or a photo-labile linker, or any other linker known in the art. The solid supports for peptide synthesis may also be polystyrene-co-polyethylene glycol resins comprising an acid labile linker, a base-labile linker, or a photo-labile linker, or any other linker known in the art. The solid supports for peptide synthesis are preferably chosen from polystyrene resins comprising an acid or base labile linker or polystyrene-co-polyethylene glycol resins comprising an acid or base labile linker. In an embodiment, the solid support for peptide synthesis may be selected from the group comprising Wang resin, Rink amide resin, ChemMatrix®, phenylacetamidomethyl (PAM) resin, Merrifield resin, and paramethyl-benzhydrylamine (pMBHA) resin. It will be understood that furan-peptides which are subsequently, e.g. after synthesizing and cleaving from the solid support, coupled, connected or linked to a further solid support, such as for instance beads, membranes, colloids, rubber or synthetic particles and the like, can be considered free furan-peptides.

The furan-peptides as taught herein may be provided in a composition. In an embodiment, the composition preferably comprises or consists of at least 60%, preferably, at least 65%, 70%, 75%, 80%, 85%, 90%, 95%, 96%, 97%, 98%, 99% or 100% of furan-peptides. For example, the composition comprises from about 60% to about 70% of furan-peptides, for example, from about 70% to about 80% of furan-peptides, for example, from about 80% to about 90% of furan-peptides, for example, the composition comprises from about 90% to about 100% of furan-peptides. In an embodiment, the composition consists of 100% of substantially pure furan-peptides.

In certain embodiments of the methods or cell-based assays as taught herein, the cell surface protein may be a GPCR and the ligand may be a peptide.

Accordingly, in certain embodiments, the present invention relates to a method for covalently binding a GPCR (e.g., GPR54) and a peptide (e.g., kisspeptin-10), the peptide being capable of specifically binding to the GPCR, the method consisting essentially of contacting living cells expressing the GPCR with the peptide comprising at least one furan moiety, thereby covalently binding the GPCR and the peptide.

As mentioned above, in certain embodiments of the methods or cell-based assays as taught herein, the ligand may be a peptide, a nucleoside, a nucleic acid, a lipid, a polysaccharide, a small molecule, or a combination thereof. In certain embodiments, the ligand may be a peptide, a nucleoside, a nucleic acid, a lipid, or a small molecule. In certain embodiments, the ligand may be a peptide, a nucleoside, a nucleic acid, or a lipid. In certain embodiments, the ligand may be a peptide, a nucleoside, a nucleic acid, or a small molecule. In certain embodiments, the ligand may be a peptide, a nucleoside, or a nucleic acid.

In certain embodiments, the ligand as taught herein may be a nucleoside. Suitable non-limiting examples of nucleosides include cytidine, deoxycytidine, uridine, deoxyuridine, adenosine, deoxyadenosine, guanosine, deoxyguanosine, thymidine, 5-methyluridine, and inosine.

In certain embodiments, the ligand as taught herein may be a nucleic acid such as RNA or DNA.

In certain embodiments, a furan moiety may be incorporated in a nucleoside (and thus in a nucleic acid) by methods known in the art. For instance, a furan moiety may be incorporated in a nucleoside by alkylation of the 2'-OH (Jawalekar et al., 2011, Chem. Commun., 47, 2796-2798). Alternatively, a furan carboxylic acid can be coupled through amide bond formation to a 2' amino nucleoside (Op de Beeck and Madder, 2012, JACS, 134, 10737-10740), or via reaction of a 2'-amino nucleoside with furfurylisocyanate (i.e., compound of Formula IIIi) (Op de Beeck and Madder, 2012, supra). Finally, a furan moiety can be introduced in the 5-position of a nucleoside base through Stille cross coupling of stannylated furan with commercially available 5-iodo-2'-deoxyuridine (Carrette at al., 2013, Bioconjugate Chem., 2008-2014).

In certain embodiments, the ligand as taught herein may be a lipid. Suitable non-limiting examples of lipids include lysophosphatidic acid and sphingosine-1-phosphate.

In certain embodiments of the methods or cell-based assays, as taught herein, the ligand may be lysophosphatidic acid and the cell surface protein may be one or more, such as two, three, four, five or six, lysophospholipid receptors selected from lysophosphatidic acid receptor 1 (LPAR1 or EDG2), lysophosphatidic acid receptor 2 (LPAR2 or EDG4), lysophosphatidic acid receptor 3 (LPAR3 or EDG7), lysophosphatidic acid receptor 4 (LPAR4 or GPR23), lysophosphatidic acid receptor 5 (LPAR5 or GPR92), or lysophosphatidic acid receptor 6 (LPAR6 or P2RY5).

In certain embodiments of the methods or cell-based assays, as taught herein, the ligand may be sphingosine-1-phosphate and the cell surface protein may be one or more, such as two, three, four of five, lysophospholipid receptors selected from sphingosine-1-phosphate receptor 1 (S1PR1 or EDG1), sphingosine-1-phosphate receptor 2 (S1PR2 or EDG5), sphingosine-1-phosphate receptor 3 (S1PR3 or EDG3), sphingosine-1-phosphate receptor 4 (S1PR4 or EDGE), or sphingosine-1-phosphate receptor 5 (S1PR5 or EDGE).

In certain embodiments, a furan moiety may be incorporated in a lipid by methods known in the art. For instance, a furan moiety may be incorporated in a lipid via esterification of the lipid with a furan fatty acid. Furan fatty acids may occur as minor compounds in the lipids of different food samples (Vetter and Wendlinger, 2013, Lipid Technology, 25, 7-10). Methods for the isolation of furan lipids and furan fatty acids of foods, such as avocado, have been described, for instance in U.S. Pat. No. 6,582,688.

In certain embodiments, the ligand as taught herein may be a polysaccharide.

In certain embodiments, a furan moiety may be incorporated in a polysaccharide by methods known in the art. For instance, a furan moiety may be incorporated in a polysaccharide via reaction of furan carboxylic acids or furfurylisocyanate with amino groups of aminoglycoside moieties.

In certain embodiments, the ligand as taught herein may be a small molecule. In certain embodiments, the small molecule may be a drug, a pesticide, or a cell signaling molecule.

In certain embodiments, a furan moiety may be incorporated in a small molecule by methods known in the art. For instance, a furan moiety may be incorporated in a small molecule by reacting a small molecule with a commercially available furan derivative (e.g., compounds of Formula Ma, IIIb, IIIc, IIId, IIIe, IIIf, IIIh, IIIg, IIIi, IIIj, or IIIk as defined herein) For instance, depending on the functional group availability, a commercially available furan derivative such as furan carboxylic acids or furfurylisocyanate can be incorporated into a small molecule by methods known in the art such as esterification, amide bond formation, aryl-aryl coupling, or urea bond formation.

As mentioned above, a first aspect provides a method for covalently binding a cell surface protein and a ligand, the ligand being capable of specifically binding to the cell surface protein, the method consisting essentially of contacting living cells expressing the cell surface protein with the ligand comprising at least one furan moiety, thereby covalently binding the cell surface protein and the ligand.

The cells as used in the methods or cell-based assays as taught herein are living (viable) cells.

The terms "living cells" or "viable cells" as used herein refer to cells that can be qualified as viable by tests known per se, and more particularly refer to cells that are capable of dividing and proliferating. Where cells are said to be living or viable, a sizeable fraction of the tested cells may test as viable, e.g., at least about 20%, at least about 40%, preferably at least about 50%, more preferably at least about 60%, even more preferably at least about 70%, still more preferably at least about 80%, yet more preferably at least about 90%, and still more preferably at least about 95% and up to 100% of the tested cells may test as viable.

Viability of cells may be measured using techniques known in the art. Techniques for determining viability or cell survival are commonly referred to as viability assays. For instance, the viability of cells may be measured using conventional dye exclusion assays, such as Trypan Blue exclusion assay or propidium iodide exclusion assay. In such assays, viable cells exclude the dye and hence remain unstained, while non-viable cells take up the dye and are stained. The cells and their uptake of the dye can be visualised and revealed by a suitable technique (e.g., conventional light microscopy, fluorescence microscopy, flow cytometry), and viable (unstained) and non-viable (stained)

cells in the tested sample can be counted. Cell survival can be conveniently expressed as the absolute number of living cells, or as cell viability (i.e., the ratio or proportion (%) of viable cells to total (i.e., sum of viable and non-viable) cells).

In certain embodiments, the cells as taught herein may be animal cells, preferably warm-blooded animal cells, more preferably mammalian cells, such as human cells or non-human mammalian cells, and most preferably human cells.

In certain embodiments, the cells as intended herein may be cells present in vivo, such as cells in tissues or bodily fluids present inside the body.

In certain embodiments, the cells as intended herein may be cells present ex vivo, such as cells in tissues or homogenized tissues.

In certain embodiments, the cells as intended herein may be cells grown or cultured in vitro. Preferably, the cells may be cells grown or cultured in vitro.

In certain embodiments, the cells as taught herein may be obtained from a biological sample of a subject.

The term "subject" or "patient" are used interchangeably and refer to animals, preferably warm-blooded animals, more preferably vertebrates, and even more preferably mammals specifically including humans and non-human mammals, that have been the object of treatment, observation or experiment. The term "mammal" includes any animal classified as such, including, but not limited to, humans, domestic and farm animals, zoo animals, sport animals, pet animals, companion animals and experimental animals, such as, for example, mice, rats, hamsters, rabbits, dogs, cats, guinea pigs, cattle, cows, sheep, horses, pigs and primates, e.g., monkeys and apes. Particularly preferred are human subjects, including both genders and all age categories thereof.

Non-human animal subjects may also include prenatal forms of animals, such as, e.g., embryos or foetuses. Human subjects may also include foetuses, but by preference not embryos.

The term "biological sample" or "sample" as used herein generally refers to a sample obtained from a biological source, e.g., from an organism, organ, tissue or cell culture, etc. A biological sample of an animal or human subject refers to a sample removed from an animal or human subject and comprising cells thereof. The biological sample of an animal or human subject may comprise one or more tissue types and cells of one or more tissue types. Methods of obtaining biological samples of an animal or human subject are well known in the art, e.g., tissue biopsy or drawing blood.

In an embodiment, the cells may be obtained from a healthy subject. This may advantageously allow identifying and/or studying cell surface protein-ligand interactions in a healthy subject.

In another embodiment, the cells may be obtained from a diseased subject. In certain embodiments, the cells may be obtained from a subject who has a proliferative disease or disorder, for instance a tumour or cancer. In certain embodiments, the cells may be obtained from a subject who has an infectious disease. In certain embodiments, the cells may be obtained from a subject who has a genetic disease. In certain embodiments, the cells may be obtained from a subject who has a metabolic disease. In certain embodiments, the cells may be obtained from a subject who has a respiratory disease. In certain embodiments, the cells may be obtained from a subject who has a rare disease. In certain embodiments, the cells may be obtained from a subject who has an auto-immune disease.

The term "proliferative disease or disorder" generally refers to any disease or disorder characterized by neoplastic cell growth and proliferation, whether benign, pre-malignant, or malignant. The term proliferative disease generally includes all transformed cells and tissues and all cancerous cells and tissues. Proliferative diseases or disorders include, but are not limited to abnormal cell growth, benign tumours, premalignant or precancerous lesions, malignant tumours, and cancer.

As used herein, the terms "tumour" or "tumour tissue" refer to an abnormal mass of tissue resulting from excessive cell division. A tumour or tumour tissue comprises "tumour cells" which are neoplastic cells with abnormal growth properties and no useful bodily function. Tumours, tumour tissue and tumour cells may be benign, pre-malignant or malignant, or may represent a lesion without any cancerous potential. A tumour or tumour tissue may also comprise "tumour-associated non-tumour cells", e.g., vascular cells which form blood vessels to supply the tumour or tumour tissue, or immune cells as part of the tumour microenvironment. Non-tumour cells may be induced to replicate and develop by tumour cells, for example, the induction of angiogenesis in a tumour or tumour tissue.

As used herein, the term "cancer" refers to a malignant neoplasm characterized by deregulated or unregulated cell growth.

The term "infectious disease" generally refers to any disease resulting from an infection.

The term "infection" generally refers to an invasion of a subject's body tissues by disease-causing agents, their multiplication, and the reaction of the subject's tissues to these organisms and the toxins they produce. Disease-causing agents or infectious agents include bacteria; viruses; viroids; prions; nematodes such as parasitic roundworms and pinworms; arthropods such as ticks, mites, fleas, and lice; fungi such as ringworm; and other macroparasites such as tapeworms and other helminths.

In certain embodiments, the cells as taught herein may be primary cells. In certain embodiments, the cells as taught herein may be obtained from a primary cell culture.

The term "primary cells" generally refers to cells that are grown or cultured directly after isolation from a subject.

The term "primary cell culture" refers to a cell culture obtained by growing or culturing cells directly after their isolation from a subject. Primary cell cultures typically have a limited lifespan.

In certain embodiments, the cells as taught herein may be obtained from an established cell line.

The terms "established cell line" or "immortalized cell line" generally refer to a cell line that has acquired the ability to proliferate indefinitely (for instance through random mutation or deliberate modification, such as artificial expression of the telomerase gene).

Established cell lines and primary cells are commercially available, for instance from the ATCC Cell Biology Collection, the European Collection of Authenticated Cell Cultures (ECACC), or the Biobank (Creative Bioarray, NY, USA).

In certain embodiments, the cells as taught herein may be obtained from a human cell line. In certain embodiments, the cells as taught herein may be obtained from a non-human mammalian cell line, such as a mouse cell line.

In certain embodiments, the cells as taught herein may be obtained from a cell line derived from normal (healthy) tissue or cells. In certain embodiments, the cells as taught herein may be obtained from a cell line derived from a diseased tissue or cells.

In certain embodiments, the cells as taught herein may be obtained from a normal (healthy) cell line. In certain embodiments, the cells as taught herein may be obtained from a cancer cell line, a tumour cell line, an infectious disease cell line, a metabolic disease cell line, a genetic disease cell line, a respiratory disease cell line, or a rare disease cell line.

Suitable non-limiting examples of normal human cell lines include human umbilical vein endothelial cells (HUVECs), T- or B-cells form healthy donors, human aortic smooth muscle cells (HAOSMCs), human bronchial epithelial cells (HBEpCs), human mammary epithelial cells (HMEpC), and human lung cell lines such as MRC-5.

Suitable non-limiting examples of normal mouse cell lines include NIH 3T3 fibroblasts, mouse embryonic fibroblasts (MEFs), Ba/F3 B-cell line, mouse T-cells, and Sol 8 myoblast cell line.

Suitable non-limiting examples of cancer human cell lines include MDA-MB-231 (breast cancer), MCF-7 (breast cancer), HeLa (cervix cancer), PC3 (prostate cancer), HEPG2 (liver cancer), Jurkat (leukemia), and HT1080 (fibrosarcoma).

Suitable non-limiting examples of cancer mouse cell lines include HEPA1-6 (liver cancer), 4T1 (breast cancer), Tramp C1-3 (prostate cancer), and B16-F10 (melanoma).

In certain embodiments of the methods or cell-based assays as taught herein, the living cells as taught herein may be normal cells (healthy cells). In certain embodiments, the cells as taught herein may be diseased cells such as cancerous cells (e.g., derived from a cancer cell line or cancer or tumour) or infected cells (e.g., derived from an infectious disease cell line or infected tissue).

In certain preferred embodiments, the cells as taught herein may be normal cells. The present inventors surprisingly found that the methods of the present invention allow covalent binding of a cell surface receptor and a ligand specifically binding to the cell surface receptor in normal cells using only the cell's own biosynthetic machinery. This is completely unexpected since in normal cells (as opposed to diseased cells) the covalent binding of the cell surface receptor and the ligand cannot be attributed to the presence of oxidative stress. The precise nature of the cellular source causing the endogenous activation remains unknown.

When the methods are performed in vitro, the living cells may be grown as an adherent monolayer on a surface or the living cells may be in cell suspension.

In certain embodiments, the cells as taught herein may be adherent, i.e., require a surface for growth, and typically grow as an adherent monolayer on said surface (i.e., adherent cell culture). Adhesion of cells to a surface, such as the surface of a tissue culture plastic vessel, can be readily examined by visual inspection under inverted microscope. Cells grown in adherent culture require periodic passaging, wherein the cells may be removed from the surface enzymatically (e.g., using trypsin), suspended in growth medium, and re-plated into new culture vessel(s). In general, a surface or substrate which allows adherence of cells thereto may be any substantially hydrophilic substrate. As known in the art, tissue culture vessels, e.g., culture flasks, well plates, dishes, or the like, may be usually made of a large variety of polymeric materials, suitably surface treated or coated after moulding in order to provide for hydrophilic substrate surfaces.

In certain embodiments, the cells as taught herein may be free-floating cells in a culture medium (suspension culture). The terms "suspension" and "cell suspension" generally refers to a heterogeneous mixture containing cells dispersed in a liquid phase. As the composition is liquid, the cells may in principle be able to, but need not, settle or sediment from the composition.

In an embodiment, the methods as taught herein consist essentially of or consist of contacting (or bringing together) living cells expressing a cell surface protein with a ligand comprising at least one furan moiety.

The term "contacting living cells expressing a cell surface protein with a ligand" as used herein refers to exposing the living cells expressing the cell surface protein to the ligand. The living cells expressing the cell surface protein are contacted with the ligand to ensure that the ligand can specifically bind to the cell surface protein expressed on the living cells.

In certain embodiments, the living cells and the ligand may be contacted for at least 1 minute. For instance, the living cells and the ligand may be contacted for at least 2 minutes, at least 3 minutes, at least 4 minutes, at least 5 minutes, at least 10 minutes, at least 15 minutes, at least 20 minutes, at least 25 minutes, at least 30 minutes, at least 35 minutes, at least 40 minutes, at least 45 minutes, at least 50 minutes, at least 55 minutes, at least 60 minutes (1 hour), at least 90 minutes (1.5 hours), at least 120 minutes (2 hours), at least 150 minutes, at least 180 minutes (3 hours), at least 240 minutes (4 hours), at least 300 minutes (5 hours), or at least 360 minutes (6 hours). Preferably, the living cells and the ligand may be contacted for at least 5 minutes such as for 10 minutes, 15 minutes, 30 minutes or 60 minutes (1 hour).

Time, as used herein, is expressed in minutes or hours. It is to be noted however that time may also be expressed in other units such as seconds.

The terms "time", "time period", and "time duration" may be used interchangeably.

In certain embodiments, the living cells and the ligand may be contacted under physiological conditions. In certain embodiments of the methods or cell-based assays as taught herein, the methods or cell-based assays as taught herein may be performed under physiological conditions. Advantageously, such conditions allow the application of the methods or cell-based assays as described herein in a cellular context, e.g., on adherent living cells or on living cells in suspension.

In certain embodiments, the methods or cell-based assays as taught herein may be performed in solution. The methods or cell-based assays as taught herein may be performed in a solution which is compatible with cell viability and in which the ligand is soluble. The solution may be any physiological solution such as cell culture media covering adherent cells or cell culture media in which cells are in suspension.

In certain embodiments, the methods or cell-based assays as described herein may be performed in an aqueous solution. In certain preferred embodiments, the living cells and the ligand may be contacted in an aqueous solution. As mentioned above, in certain embodiments, the ligands as taught herein may be provided in a solvent. In certain embodiments of the methods or cell-based assays as taught herein, the final concentration of the solvent in the aqueous solution is kept below a concentration that is toxic to the cells (e.g., for ligands dissolved in DMSO, the concentration of DMSO is kept below 0.5%, preferably below 0.2%, more preferably below 0.1%). Such final concentrations of the solvent in the aqueous solution do not compromise the viability or proliferation of the living cells.

The term "aqueous solution" generally refers to a solution in which the solvent comprises, consists essentially of, or consists of water. In certain embodiments, the aqueous solution comprises at least 0.1% of water. For example, the aqueous solution comprises at least 0.5%, at least 1%, at least 5%, at least 10%, at least 20%, at least 30%, at least 40%, at least 50%, at least 60%, at least 70%, at least 80%, at least 90%, at least 95%, or at least 99% of water. In certain embodiments, the solvent consists of water.

In certain embodiments, the aqueous solution may be a buffer such as a phosphate buffer, preferably phosphate buffered saline (PBS).

In certain embodiments, the aqueous solution may be cell culture media as known per se, such as for example liquid cell culture media. Well-known cell culture media include Dulbecco's Modified Eagles Medium (DMEM) such as high glucose (4.5 mg/ml) DMEM or low glucose (1 mg/ml) DMEM; Eagle's minimal essential medium (EMEM); Roswell Park Memorial Institute (RPMI) media; and Ham's F12 media. The cell culture media may optionally comprise GlutaMax™. The cell culture media may comprise serum such as Fetal bovine serum (FBS) or Fetal calf serum (FCS). The cell culture media may comprise serum in a concentration of at most 10%, such as at a concentration of 0.5%, 1.0%, 5.0% or 10%.

In certain preferred embodiments, the methods or cell-based assays as described herein may be performed in cell culture media, such as DMEM, EMEM, and RPMI media, optionally comprising serum, such as FBS or FCS. This advantageously allows performing the methods or cell-based assays as taught herein in the cell culture media in which the cells have been grown. In certain embodiments, the living cells and the ligand may be contacted in an aqueous solution selected from a buffer such as a phosphate buffer, preferably PBS, or culture media such as DMEM, EMEM, and RPMI media.

In certain embodiments of the methods or cell-based assays as taught herein, the ligand as taught herein may be provided in an aqueous solution. In certain embodiments, the living cells expressing the cell surface protein as taught herein may be provided in an aqeuous solution.

In certain embodiments, the methods or cell-based assays as described herein may be performed in an aqueous solution without the use of organic solvents. In certain embodiments, the methods or cell-based assays as described herein may be performed in an aqueous solution without the use of reducing agents. In certain embodiments, the methods or cell-based assays as described herein may be performed without the use of toxic additives (e.g., copper or aniline) and/or without the use of catalysts (e.g., copper or aniline) In certain embodiments, the methods or cell-based assays as described herein may be performed in an aqueous solution without the use of organic solvents and/or without the use of reducing agents and/or without the use of toxic additives and/or without the use of catalysts. Such conditions advantageously offer great potential for the applications of the methods or cell-based assays as described herein.

In certain embodiments, the methods or cell-based assays as described herein may be performed at a pH ranging from about 6 to about 8. In certain embodiments, the methods or cell-based assays as described herein may be performed at a near neutral pH (i.e., pH of about 7).

In certain embodiments, the methods or cell-based assays as described herein may be performed at a temperature ranging from about 0° C. to about 40° C., or from about 4° C. to about 40° C., or from about 10° C. to about 40° C., or from about 20° C. to about 40° C. In certain embodiments, the methods or cell-based assays as described herein may be performed at a temperature of about 37° C.

Temperature, as used herein, is expressed in degrees Celsius (° C.). It is to be noted however that temperature may also be expressed in any other suitable unit such as Kelvin (K).

In certain embodiments, the methods or cell-based assays as described herein may be performed in an aqueous solution, at near neutral pH, and at a temperature of about 37° C. Such conditions allow the application of the methods or cell-based assays as described herein under conditions which do not influence cell viability or cell functioning both in vitro and in vivo. This is in contrast to prior art methods such as photoaffinity crosslinking which require working with cell lysates or, when working with living cells, in cold buffers.

In certain embodiments, the concentration of the ligand in the aqueous solution may be at least 0.01 µM. In certain embodiments, the concentration of the ligand in the aqueous solution may be at least 0.1 µM, at least 0.5 µM, at least 1.0 µM, at least 5.0 µM, at least 10.0 µM, or at least 50.0 µM.

In certain embodiments, the concentration of the ligand in the aqueous solution may be at ranging from 0.1 µM to 100.0 µM. In certain embodiments, the concentration of the ligand in the aqueous solution may be ranging from 0.5 µM to 50.0 µM, or from 1.0 µM to 10.0 µM, or from 0.1 µm to 10.0 µM, or from 0.1 µM to 5.0 µM.

In certain embodiments, the living cells may be grown as an adherent monolayer on a surface. In certain embodiments, the living cells may be grown as an adherent monolayer on a surface to at least 50% confluency. In certain embodiments, the living cells may be grown as an adherent monolayer on a surface to at least 55%, at least 60%, at least 65%, at least 70%, at least 75%, at least 80%, at least 85%, at least 90%, or at least 95%, such as 100% confluency.

In certain embodiments of the methods or cell-based assays as taught herein, the number of the living cells contacted with the ligand may be between about $1\times10^3$ and about $1\times10^{11}$, or between about $1\times10^4$ and about $1\times10^{10}$, or between about $1\times10^5$ and about $1\times10^9$ cells. In certain embodiments, the number of the living cells contacted with the ligand may be between about $1\times10^5$ and about $1\times10^7$ cells. In certain embodiments, the number of the living cells contacted with the ligand may be between about $1\times10^5$ and about $5\times10^6$ cells.

In an embodiment, the method as taught herein may consist essentially of or may consist of contacting living cells expressing the cell surface protein with the ligand comprising at least one furan moiety in an aqueous solution, wherein the living cells are grown as an adherent monolayer on a surface and the concentration of the ligand in the aqueous solution is ranging from 0.01 µM to 100.0 µM. For instance, the method as taught herein may consist essentially of or may consist of contacting living cells expressing the cell surface protein with the ligand comprising at least one furan moiety in an aqueous solution, wherein the living cells are grown as an adherent monolayer on a surface, and the concentration of the ligand in the aqueous solution is ranging from 0.1 µM to 100.0 µM, from 0.5 µM to 50.0 µM, from 1.0 µM to 10.0 µM, from 0.1 µm to 10.0 µM, or from 0.1 µM to 5.0 µM. Preferably, the method as taught herein may consist essentially of or may consist of contacting living cells expressing the cell surface protein with the ligand comprising at least one furan moiety in an aqueous solution, wherein the living cells are grown as an adherent monolayer on a surface, and the concentration of the ligand in the aqueous solution is ranging from 0.1 µM to 5.0 µM.

In certain embodiments of the methods or cell-based assays as taught herein, the furan moiety (of the ligand) may be oxidized by endogenous activation. The endogenous activation advantageously allows the covalently binding of a cell surface protein and a ligand without the need for any exogenous (chemical or physical) activation.

As used herein the term "endogenous" refers to originating from or produced by a cell, tissue, or organism.

As used herein the term "exogenous" refers to caused or produced by factors external to a cell, tissue, or organism.

In certain embodiments, the furan moiety (of the ligand) is oxidized by the cells. In certain embodiments, the furan moiety (of the ligand) is oxidized by the cells through endogenous activation. In certain embodiments, the furan moiety (of the ligand) is oxidized by a cellular source.

In certain embodiments, the furan moiety (of the ligand) is oxidized by a cellular source through endogenous activation. The precise nature of the cellular source is unknown.

The present inventors have found that when living cells expressing a cell surface protein are contacted with a ligand which specifically binds the cell surface protein, covalent binding between the cell surface protein and the ligand occurs. This suggests that specific binding of the ligand to the cell surface protein on the living cells is sufficient to cause activation of the furan moiety.

In certain embodiments of the methods or cell-based assays as taught herein, the endogenous activation may occur at the extracellular space of the cell membrane.

In certain embodiments of the methods or cell-based assays as taught herein, the cell surface protein may comprise at least one amine group, hydroxyl group, sulfhydryl group, imidazole group and/or indole group. In certain embodiments of the methods or cell-based assays as taught herein, the oxidized furan moiety of the ligand may react with the amine group, hydroxyl group, sulfhydryl group, imidazole group and/or indole group of the cell surface protein. In certain embodiments, the furan moiety of the ligand may be oxidized by endogenous activation, the cell surface protein may comprise at least one amine group, hydroxyl group, sulfhydryl group, imidazole group and/or indole group, and the oxidized furan moiety of the ligand may react with the amine group, hydroxyl group, sulfhydryl group, imidazole group and/or indole group of the cell surface protein.

In certain embodiments of the methods or cell-based assays as taught herein, the cell surface protein may comprise a binding site comprising at least one nucleophile. Such a nucleophile advantageously allows binding with the oxidized furan moiety. Hence, in certain embodiments, the oxidized furan moiety of the ligand may react with the nucleophile of the binding site of the cell surface protein. In certain embodiments, the furan moiety of the ligand may be oxidized by endogenous activation, the cell surface protein may comprise a binding site comprising a nucleophile, and the oxidized furan moiety of the ligand may react with the nucleophile of the binding site of the cell surface protein.

In certain embodiments of the methods or cell-based assays as taught herein, the nucleophile may be an amine group, a hydroxyl group, a sulfhydryl group, an imidazole group and/or an indole group. In certain embodiments, the cell surface protein may comprise a binding site comprising at least one amine group, hydroxyl group, sulfhydryl group, imidazole group and/or indole group. Cell surface proteins comprising a binding site comprising a nucleophile, such as amine group, hydroxyl group, sulfhydryl group, imidazole group and/or indole group, advantageously allow the cross-linking of the cell surface protein and the ligand.

In certain embodiments, the furan moiety (of the ligand) is oxidized without the addition of an exogenous activation signal. In certain embodiments, the furan moiety (of the ligand) is oxidized without the addition of an exogenous oxidative reagent. The example section illustrates that the present methods allow for the first time chemical crosslinking (covalent binding) of a (modified, i.e., furan-containing) ligand on its unmodified endogenous receptor in cells without any form of exogenous intervention (e.g., chemical activation signal such as NB S, or physical activation signal such as UV-light).

The methods illustrating the present invention allow covalent in situ labeling of cell surface proteins, e.g. in diagnostics, as a cheap, reliable alternative to antibodies. The present methods allow the detection and/or in situ visualization of cell surface proteins, thereby allowing to study internalization, trafficking and/or diffusion characteristics of the cell surface proteins in the cell membrane.

A further aspect relates to a method for detecting a cell surface protein covalently bound to a ligand, the ligand being capable of specifically binding to the cell surface protein, the method consisting essentially of or consisting of:

performing the methods as taught herein, and
detecting the cell surface protein covalently bound to the ligand.

Accordingly, certain embodiments provide a method or cell-based assay for detecting a cell surface protein covalently bound to a ligand, the ligand being capable of specifically binding to the cell surface protein, the method consisting essentially of or consisting of contacting living cells expressing the cell surface protein with the ligand comprising at least one furan moiety, thereby covalently binding the cell surface protein and the ligand, and detecting the cell surface protein covalently bound to the ligand.

By performing the methods as taught herein, the cell surface protein and the ligand are covalently bound. Optionally, the ligand may comprise a label, which may facilitate the detection (e.g., visualization) of the cell surface protein. The step of detecting the cell surface protein covalently bound to the ligand may be performed by any adequate technique known to the skilled person. In certain embodiments, the step of detecting the cell surface protein covalently bound to the ligand may be performed by flow cytometry such as Fluorescence-activated cell sorting (FACS); by microscopy such as fluorescence confocal microscopy, epifluorescence microscopy, or live cell imaging; gel-electrophoresis; Western blot; immunoassays such as enzyme-linked immunosorbent assay (ELISA); mass spectrometry such as matrix-assisted laser desorption/ionization-time of flight (MALDI-TOF), electro spray ionization-mass spectrometry (ESI-MS), liquid chromatography-mass spectrometry (LC-MS), and orbitrap mass spectrometry; or a combination thereof.

The wordings "detecting the cell surface protein covalently bound to the ligand", "determining the presence of a covalently bound complex of the cell surface protein and the ligand" and "determining the covalent bond between the ligand and the cell surface protein" may be used interchangeably herein.

The methods of the invention may be used to identify, for a known ligand, a cell surface protein to which the ligand is capable of specifically binding thereto. Hence, in an embodiment, the present invention relates to the use of the methods for covalently binding a cell surface protein and a peptide as taught herein, for identifying, for a known ligand, a cell surface protein to which the ligand is capable of specifically binding thereto. The present inventors further found that the cell-based assays as taught herein allow identifying target cell surface proteins of biologically active orphan ligands, such as orphan peptides or small molecules, without the requirement for exogenous activation. For instance, the present cell-based assays allow to screen peptide libraries generated by standard solid phase peptide synthesis and to identify the cell surface receptors via mass spectrometry-based sequencing if a covalently bound complex is present.

Accordingly, a further aspect provides a cell-based assay for identifying, for a known ligand, a cell surface protein to which the ligand is capable of specifically binding thereto, the ligand comprising at least one furan moiety, the cell-based assay consisting essentially of or consisting of:
  contacting living cells with the ligand;
  determining the presence of a covalently bound complex of the cell surface protein and the ligand; and
  identifying the cell surface protein if the covalently bound complex is present.

In certain embodiments, the step of determining the presence of a covalently bound complex of the cell surface protein and the ligand may be performed by the techniques as described herein.

The step of identifying the cell surface protein may be performed by any adequate technique known to the skilled person for protein mass spectrometry (MS) analysis, preferably by gel electrophoresis, gas chromatography-mass spectrometry (GC-MS), liquid chromatography-mass spectrometry (LC-MS), high performance liquid chromatography-mass spectrometry (HPLC-MS), reversed phase high performance liquid chromatography-mass spectrometry (RP HPLC-MS), matrix-assisted laser desorption/ionization-time of flight (MALDI-TOF), electro spray ionization-mass spectrometry (ESI-MS), inductively coupled plasma-mass spectrometry (ICP-MS), accelerator mass spectrometry (AMS), thermal ionization-mass spectrometry (TI-MS), orbitrap mass spectrometry, or spark source mass spectrometry (SS-MS), more preferably by gel electrophoresis, liquid chromatography-mass spectrometry (LC-MS), matrix-assisted laser desorption/ionization-time of flight (MALDI-TOF), or electro-spray ionization-mass spectrometry (ESI-MS). These techniques for protein mass spectrometry analysis can optionally be preceded by an enzyme proteolytic digest such as a tryptic digest.

RP-HPLC is generally used to monitor the reaction progress according to the retention time of the analytes which is related to the polarity of the analytes.

MALDI-TOF analysis may provide information on the mass of the molecules involved.

Preferably, the step of identifying the cell surface protein is performed using HPLC-MS.

Furthermore, the methods as taught herein may be used to identify, for a known cell surface protein, a ligand specifically binding to the cell surface protein. Hence, in an embodiment, the present invention relates to the use of the methods for covalently binding a cell surface protein and a ligand as taught herein, for identifying, for a known cell surface protein, a ligand specifically binding to the cell surface protein. The present inventors realized that the cell-based assays as taught herein allow identifying for a known cell surface protein a ligand which specifically binds the cell surface protein by screening ligand libraries and inferring from the finding that a covalently bound complex of the cell surface protein and the ligand is present, that the ligand specifically binds the cell surface protein.

Hence, a further aspect relates to a cell-based assay for identifying, for a known cell surface protein, a ligand specifically binding to the cell surface protein, the cell-based assay consisting essentially of or consisting of:
  contacting living cells expressing the cell surface protein with a ligand comprising at least one furan moiety;
  determining the presence of a covalently bound complex of the cell surface protein and the ligand; and
  inferring from the finding that the covalently bound complex is present that the ligand specifically binds the cell surface protein.

The methods of the invention may be used to identify a binding site of an interacting peptide-cell surface protein pair. Hence, in an embodiment, the present invention relates to the use of the methods for covalently binding a cell surface protein and a peptide as taught herein, for identifying a binding site of a cell surface protein and a peptide. The present cell-based assays can be used to gain immediate insight on the location of the peptide-cell surface protein binding site.

Accordingly, a further aspect relates to a cell-based assay for identifying a binding site of a cell surface protein and a peptide, the peptide being capable of specifically binding to the cell surface protein and the peptide comprising at least one amino acid comprising a furan moiety, wherein said amino acid comprising a furan moiety is located at position n of the peptide, the cell-based assay consisting essentially of or consisting of:
  (a) contacting living cells with the peptide;
  (b) determining the presence of a covalently bound complex of the cell surface protein and the peptide;
  (c) identifying the amino acid comprising a furan moiety as a binding site of the cell surface protein and the peptide if the covalently bound complex is present;
  (d) optionally repeating steps (a) to (c) with peptides comprising a furan moiety, wherein the amino acid comprising a furan moiety is located at position n+p of the peptides comprising a furan moiety;
wherein position n may be any amino acid of the peptides comprising a furan moiety, and wherein p is a positive or negative integer (provided position n+p is located on the peptides comprising a furan moiety).

In certain embodiments of the methods or cell-based assays as taught herein, the ligand as taught herein may be a peptide.

Accordingly, in certain embodiments, the present invention relates to a cell-based assay for identifying, for a known peptide, a cell surface protein to which the peptide is capable of specifically binding thereto, the peptide comprising at least one furan moiety, the cell-based assay consisting essentially of or consisting of:
  contacting living cells with the peptide;
  determining the presence of a covalently bound complex of the cell surface protein and the peptide; and
  identifying the cell surface protein if the covalently bound complex is present.

In certain embodiments, the present invention relates to a cell-based assay for identifying, for a known cell surface protein, a peptide specifically binding to the cell surface protein, the cell-based assay consisting essentially of or consisting of:
  contacting living cells expressing the cell surface protein with a peptide comprising at least one furan moiety;
  determining the presence of a covalently bound complex of the cell surface protein and the peptide; and
  inferring from the finding that the covalently bound complex is present that the peptide specifically binds the cell surface protein.

In certain embodiments of the methods or cell-based assays as taught herein, the cell surface protein may be a GPCR and the ligand may be a peptide.

Accordingly, in certain embodiments, the present invention relates to a cell-based assay for identifying, for a known peptide, a GPCR to which the peptide is capable of specifically binding thereto, the peptide comprising at least one furan moiety, the cell-based assay consisting essentially of or consisting of:
contacting living cells with the peptide;
determining the presence of a covalently bound complex of the GPCR and the peptide; and
identifying the GPCR if the covalently bound complex is present.

In certain embodiments, the present invention relates to a cell-based assay for identifying, for a known GPCR, a peptide specifically binding to the GPCR, the cell-based assay consisting essentially of or consisting of:
contacting living cells expressing the GPCR with a peptide comprising at least one furan moiety;
determining the presence of a covalently bound complex of the GPCR and the peptide; and
inferring from the finding that the covalently bound complex is present that the peptide specifically binds the GPCR.

In certain embodiments, the present invention relates to a cell-based assay for identifying a binding site of a GPCR and a peptide, the peptide being capable of specifically binding to the GPCR and the peptide comprising at least one amino acid comprising a furan moiety, wherein said amino acid comprising a furan moiety is located at position n of the peptide, the cell-based assay consisting essentially of or consisting of:
(a) contacting living cells with the peptide;
(b) determining the presence of a covalently bound complex of the GPCR and the peptide;
(c) identifying the amino acid comprising a furan moiety as a binding site of the GPCR and the peptide if the covalently bound complex is present;
(d) optionally repeating steps (a) to (c) with peptides comprising a furan moiety, wherein the amino acid comprising a furan moiety is located at position n+p of the peptides comprising a furan moiety;
wherein position n may be any amino acid of the peptides comprising a furan moiety, and wherein p is a positive or negative integer (provided position n+p is located on the peptides comprising a furan moiety).

A further aspect relates to an expression cassette or an expression vector comprising a nucleic acid molecule encoding a cell surface protein as defined herein and a promoter operably linked to the nucleic acid molecule. Preferably, the expression cassette or expression vector may be configured to effect expression of the cell surface protein in an animal cell, such as in a mammalian cell, including human cells and non-human mammalian cells. In certain embodiments, the expression cassette or expression vector is configured to effect expression of the cell surface protein in a human cell.

The terms "expression vector" or "vector" as used herein refers to nucleic acid molecules, typically DNA, to which nucleic acid fragments may be inserted and cloned, i.e., propagated. Hence, a vector will typically contain one or more unique restriction sites, and may be capable of autonomous replication in a defined host cell or vehicle organism such that the cloned sequence is reproducible. A vector may also preferably contain a selection marker, such as, e.g., an antibiotic resistance gene, to allow selection of recipient cells that contain the vector. Vectors may include, without limitation, plasmids, phagemids, bacteriophages, bacteriophage-derived vectors, PAC, BAC, linear nucleic acids, e.g., linear DNA, viral vectors, etc., as appropriate (see, e.g., Sambrook et al., 1989; Ausubel 1992). Expression vectors are generally configured to allow for and/or effect the expression of nucleic acids or ORFs introduced thereto in a desired expression system, e.g., in vitro, in a host cell, host organ and/or host organism. For example, expression vectors may advantageously comprise suitable regulatory sequences.

A further aspect provides a kit comprising: a ligand as taught herein comprising at least one furan moiety; an expression vector comprising a nucleic acid molecule encoding a cell surface protein as taught herein; and components or instructions for covalently binding the cell surface protein and the ligand according to the methods as taught herein. In embodiments, the kits may comprise: a ligand as taught herein comprising at least one furan moiety; an expression vector comprising a nucleic acid molecule encoding a cell surface protein as taught herein; and instructions for covalently binding the cell surface protein and the ligand according to the methods as taught herein. In particular embodiments, the kits may comprise instructions for covalently binding the cell surface protein and the ligand according to the methods as taught herein.

In certain embodiments, the kits may comprise: a peptide comprising at least one furan moiety; an expression vector comprising a nucleic acid molecule encoding a cell surface protein as taught herein; and components or instructions for covalently binding the cell surface protein and the peptide according to the methods as taught herein. In certain embodiments, the kits may comprise: a peptide comprising at least one furan moiety; an expression vector comprising a nucleic acid molecule encoding a cell surface protein as taught herein; and instructions for covalently binding the cell surface protein and the peptide according to the methods as taught herein. In particular embodiments, the kits may comprise instructions for covalently binding the cell surface protein and the peptide according to the methods as taught herein.

A further aspect provides a kit comprising a ligand comprising at least one furan moiety, living cells expressing a cell surface protein, and components or instructions for covalently binding the cell surface protein and the ligand according to the methods as taught herein. In embodiments, the kits comprise a ligand comprising at least one furan moiety, living cells expressing a cell surface protein, and instructions for covalently binding the cell surface protein and the ligand according to the methods as taught herein. In particular embodiments, the kits comprise instructions for covalently binding the cell surface protein and the ligand according to the methods as taught herein.

In certain embodiments, the kits comprise a peptide comprising at least one furan moiety, living cells expressing a cell surface protein, and components or instructions for covalently binding the cell surface protein and the peptide according to the methods as taught herein. In certain embodiments, the kits comprise a peptide comprising at least one furan moiety, living cells expressing a cell surface protein, and instructions for covalently binding the cell surface protein and the peptide according to the methods as taught herein. In particular embodiments, the kits comprise instructions for covalently binding the cell surface protein and the peptide according to the methods as taught herein.

EXAMPLES

Materials and Methods

Materials

Fmoc-ß-(2-furyl)-Ala-OH, Fmoc-L-4-Benzoylphenylalanine-OH were purchased from Peptech. All other amino acids, as well as Rink Amide AM (200-400 mesh), coupling reagent 2-(1H-benzotriazol-1-yl)-1,1,3,3-tetramethyluronium hexafluorophosphate (HBTU), trifluoroacetic acid (TFA) and biotin-dPEG(4)-COOH were purchased from Iris Biotech. ChemMatrix was obtained from Biotage. D-biotin was purchased from Chem-Impex International. Coupling reagent 1-Cyano-2-ethoxy-2-oxoethylidenaminooxy)dimethylamino-morpholino-carbenium hexafluorophosphate (COMU) was purchased from Novabiochem. Peptide synthesis grade DMF was purchased from Biosolve. Dichloromethane, methanol, N,N-Diisopropylethylamine (DIPEA), dimethylsulfoxide (DMSO) and triisopropylsilane (TIS) were obtained from Sigma Aldrich.

Rabbit anti-GPR54 was purchased from Alomone Labs (cat. nr. AKR-001). IRDye conjugated streptavidin and secondary antibodies were obtained from Li-Cor Biotechnology. Dulbecco's Modified Eagle Medium (DMEM), Dulbecco's Phosphate Buffered Saline (DPBS) and Fetal bovine serum (FBS) were purchased from Gibco.

N-bromosuccinimide, N-acetyl cysteine, and streptavidin-agarose resin were obtained from Sigma Aldrich.

Peptide Synthesis

The different kisspeptin-10 peptides were synthesized by standard Fmoc-based solid-phase peptide synthesis on a Syro II automated peptide synthesizer (Multisyntech), using either Rink Amide AM (200-400 mesh) or Rink Amide ChemMatrix as solid support. The peptide chain was assembled using HBTU as coupling reagent. For Fmoc-deprotection, a 3' treatment with 40% piperidine in DMF was used, followed by a 12' treatment with 20% piperidine in DMF. The furan and benzophenone moiety were introduced using the commercially available unnatural amino acids Fmoc-ß-(2-furyl)-Ala-OH and Fmoc-L-4-Benzoylphenylalanine-OH. These amino acids were coupled manually to the peptide chain using COMU as coupling reagent.

All peptides were biotinylated after automated synthesis using either biotin or biotin-dPEG(4)-COOH, with COMU as coupling reagent in the presence of DIPEA. Peptides were cleaved off with TFA/TIS/H2O (95/2.5/2.5) during 2 h and precipitated with cold methyl tert-butyl ether and analysed by RP-HPLC and ESI-MS or MALDI-MS.

HPLC and Mass Analysis

LC-ESI-MS analysis on peptides was performed on an Agilent 1100 Series HPLC instrument equipped with a Phenomenex Kinetex C18 column (150 mm×4.6 mm, 5 µm) at 35° C., using a flow rate of 1.5 mL/min. The column was eluted with a gradient, starting with 100% $H_2O$ containing 5 mM NH4OAC up to 100% acetonitrile. A G1946C ES-MSD mass detector was directly coupled to the column.

RP-HPLC analysis was also performed on an Agilent 1100 Series HPLC instrument, equipped with a Phenomenex Luna C18(2) column (250 mm×4.6 mm, 5 µM) at 35° C., using a flow rate of 1 mL/min. The column was eluted with a gradient, starting with 100% $H_2O$ containing 0.1% TFA up to 100% acetonitrile. The collected fractions were subsequently analysed on a Voyager-DE STR Biospectrometry Workstation (Applied Biosystems), with α-cyano-4-hydroxycinnamic acid as matrix.

Cell Culture

All used cell lines were grown in Dulbecco's Modified Eagle Medium, with high glucose content (4.5 mg/mL), no pyruvate and supplemented with Glutamax and 10% (v/v) heat inactivated Fetal bovine serum (FBS) plus antibiotics in a humidified atmosphere with 5% $CO_2$ at 37° C. The HEK-myc-KISS1R cell line was kindly provided by Kaiser U. B. of the Brigham and Women's Hospital in Boston (Min et al., 2013, Mol. Endocrinol., 28, 16-27).

Crosslinking Experiments Followed by Western Blot

Crosslinking Furan-Peptides to Cellular Receptor in PBS

Cells were seeded on a 56.7 $cm^2$ or a 6-well tissue culture treated plate until confluency in normal growth medium. Cell culture medium was replaced by cold PBS and the cells were incubated with the peptide 2 or 4 (1 µM or as indicated) during 1 h at 4° C. In a competition experiment, 10 µM (or as indicated) of 1 was added simultaneously. After incubation, 1 equivalent of NBS was added and reaction occurred for 1 h.

Crosslinking Benzophenone-Peptide to Cellular Receptor in PBS

Cells were seeded on a 56.7 $cm^2$ or a 6-well tissue culture treated plate. Cell culture medium was replaced by cold PBS and the cells were incubated with the peptide 3 or 5 (1 µM or as indicated) during 1 h at 4° C. In a competition experiment, 10 µM (or as indicated) of 1 was added simultaneously. After incubation, cells were irradiated with UV light (360 nm) for 30 minutes on ice.

Crosslinking Furan-Peptides to Cellular Receptor in Growth Medium

Cells were seeded on a 56.7 $cm^2$ or a 6-well tissue culture treated plate until confluency and incubated with the peptides during 30 minutes at 37° C. in growth medium with indicated % of serum. A concentration of 1 µM of the furan-modified peptide was used. When not relying on endogenous cellular oxidation source, furan oxidation was achieved by adding 1 eq. NBS for 30 minutes at 37° C. In a competition experiment, 10 µM of 1 was added simultaneously.

Cell Lysis and Western Blot Analysis

After crosslinking, cells were harvested using trypsinization. The cell pellet was washed with PBS and lysed with lysis buffer (1% CHAPS, 7M urea, 2M thiourea, protease inhibitors, 50 mg/mL DTT). The cell lysate was sonicated and cell debris was removed by centrifugation at 13,000 rpm for 10 minutes at 4° C. Protein concentration was determined using the Bradford assay (Biorad). 40 µg total protein was analysed on a 10% SDS-polyacrylamide gel. The separated proteins in the gel were transferred to a nitrocellulose membrane. The membrane was incubated overnight at 4° C. with rabbit anti-GPR54 and sequentially incubated with anti-rabbit IRDye 800 and streptavidin IRDye 680 for 1 h at room temperature. Detection involved scanning of the membrane with an Odyssey Infrared Imaging System (LI-COR Biosciences).

Example 1: Synthesis of Furan-Peptides 2, 4, 6 and 7 and Peptides 1, 3 and 5

As model system, the kisspeptin-10 peptide (FIG. 4, compound 1) and its native membrane receptor G-protein coupled receptor (GPCR) GPR54 (also called AXOR12 or KISS1R) was used. This model is considered a physiologically relevant model of a low abundant transient protein-protein complex, since it is shown that in cells the receptor GPR54 undergoes dynamic post-translational modification and both the receptor and the cell surface receptor-ligand complex turnover rapidly.

The KISS1 gene encodes a 145 amino acid protein that undergoes proteolysis to metastatin and further truncation to 14, 13 or 10 amino acid containing carboxy-terminal fragments (the so-called kisspeptins), showing biological activity (Kotani et al., 2001, J. Biol. Chem., 276, 34631-6; Ohtaki et al., 2001, Nature, 411, 613-7).

Figure 5:
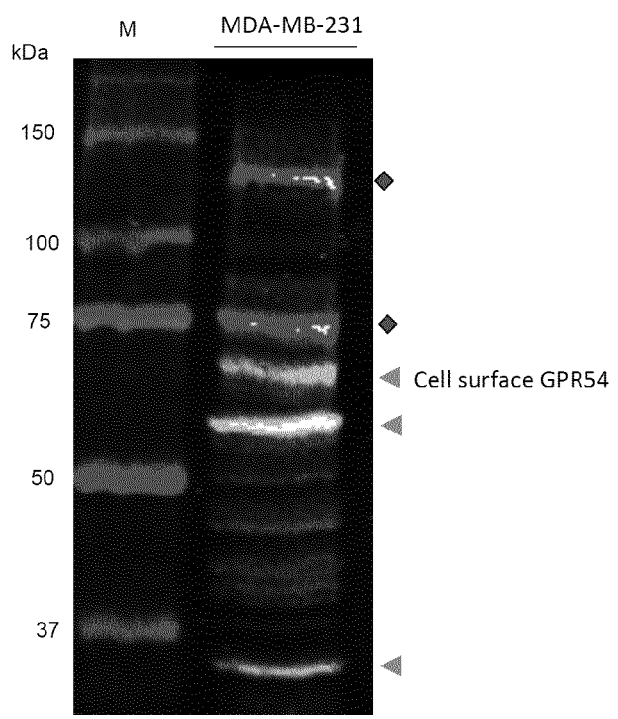
FIG. 5 represents a photograph of a Western blot illustrating the different forms of receptor GPR54 in MDA-MB-231 cells. Western Blot of cell lysate of MDA-MB-231 cells using an antibody against GPR54 (arrowheads) and biotin-responsive streptavidin (diamonds). Receptor GPR54 is present as three subspecies of 37 kDa, 54 kDa, and 72 kDa (arrowheads). These subspecies represent different states of maturation via glycosylation and the 72 kDa is the receptor form presented at the cell surface. The signals from endogenous biotinylated proteins are shown (diamonds) as reference for the background signal in all biotin probing results. The MW of the shown marker proteins (M) is indicated.

In an initial experiment, the different forms of GPR54 in MDA-MB-231, a breast cancer cell line that endogenously expresses GPR54, were analysed. Three GPR54 forms were observed with molecular sizes of 37, 54 and 72 kDa (FIG. 5, arrows). The largest form represents the mature glycosylated GPR54, present at the cell surface. In the binding experiments below, the formation of a ligand-cell surface receptor complex, namely a kisspeptin-GPR54 complex, is visualized by probing biotin (see below for kisspeptin-10 comprising biotin). FIG. 5 further shows that untreated MDA-MB-231 already contains two endogenous biotinylated proteins (indicated by diamonds in all figures). It is assumed that these proteins are endogenously biotinylated carboxylases with an apparent molecular weight (MW) of ca. 75 kDa (i.e., present at a slightly higher molecular weight than the covalently bound ligand-cell surface receptor complex (see Example 2)), and of 130 kDa. These background signals were used as loading control.

Kisspeptin-10 peptide and analogues were chemically synthesized as described in Materials and methods, Peptide synthesis). The HPLC chromatograms and mass spectra of compound 1 (Chemical Formula: $C_{63}H_{83}N_{17}O_{14}$, Exact Mass: 1301.63 Da, Molecular Weight: 1302.46 Da), 2 (Chemical Formula: $C_{69}H_{94}N_{18}O_{17}S$, Exact Mass: 1478.68 Da, Molecular Weight: 1479.68 Da), 3 (Chemical Formula: $C_{78}H_{100}N_{18}O_{17}S$, Exact Mass: 1592.72 Da, Molecular Weight: 1593.83 Da), 4 (Chemical Formula: $C_{71}H_{95}N_{19}O_{16}S$, Exact Mass: 1501.69 Da, Molecular Weight: 1502.72 Da), 5 (Chemical Formula: $C_{80}H_{101}N_{19}O_{16}S$, Exact Mass: 1615.74 Da, Molecular Weight: 1616.87 Da), 6 (Chemical Formula: $C_{80}H_{115}N_{19}O_{22}S$, Exact Mass: 1725.82 Da, Molecular Weight: 1726.97 Da), and 7 (Chemical Formula: $C_{80}H_{115}N_{19}O_{22}S$, Exact Mass: 1725.82 Da, Molecular Weight: 1726.97 Da) were obtained and illustrated the quality of compounds 1 to 7 (results not shown). HPLC and mass analysis was performed as described in Materials and methods, HPLC and mass analysis.

Figure 4:
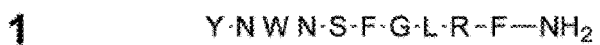
FIG. 4 represents an overview illustrating the sequence of kisspeptin 10 (compound 1) and analogues thereof (compounds 2 to 7). Except for compound 1, the peptides were labeled at the N-terminus using either biotin (2-5) or biotin-dPEG(4) (6 and 7). In peptides 2, 4, 6, 7 furylalanine (FUA) substitutes the amino acid at position 3 (in 2, 6, and 7) or position 1 (in 4). Peptides 3 and 5 contain benzoylphenylalanine (BPA).
Figure 4:
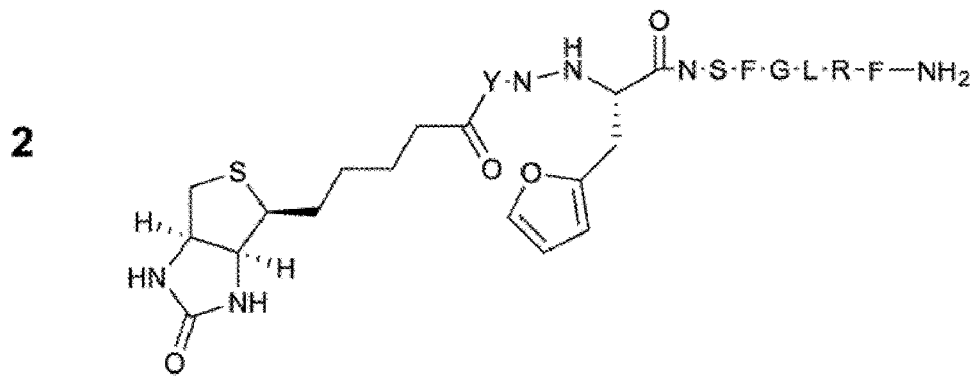
Figure 4:
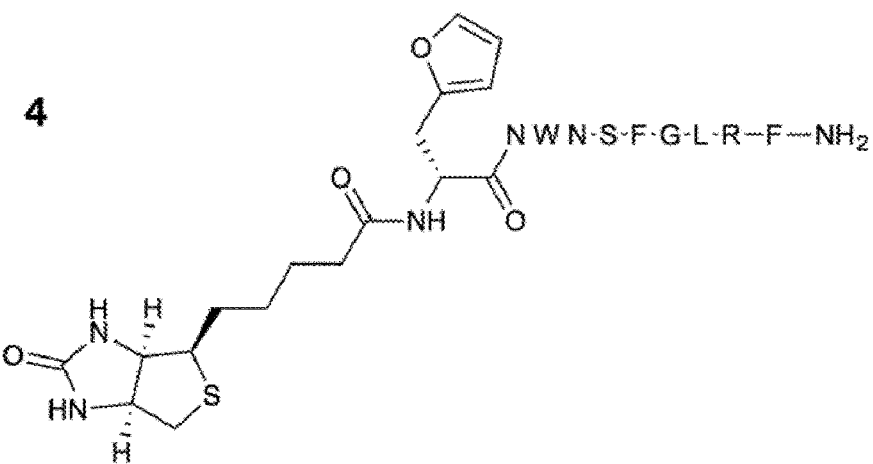
Figure 4:
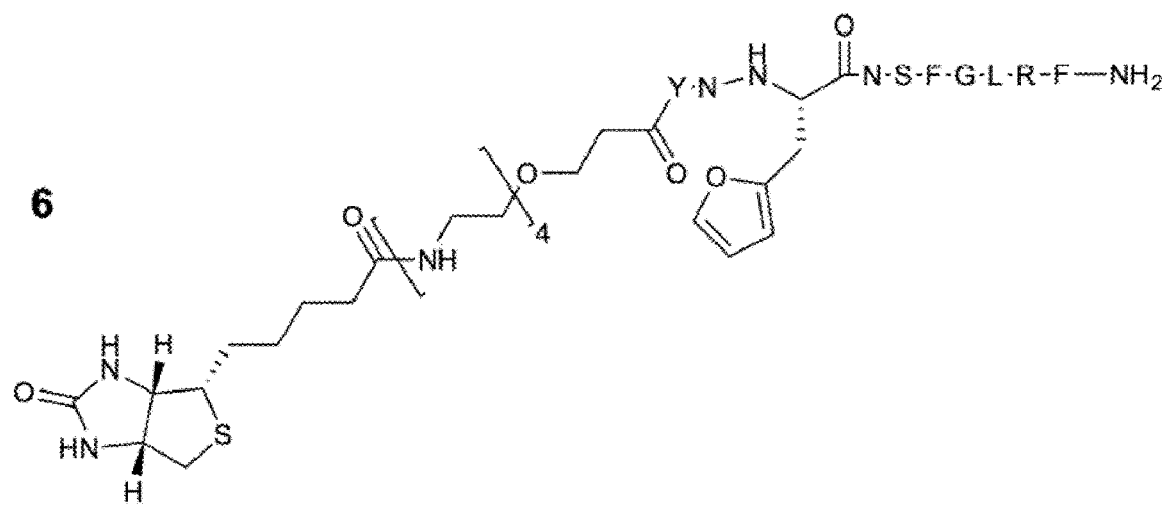
Figure 4:
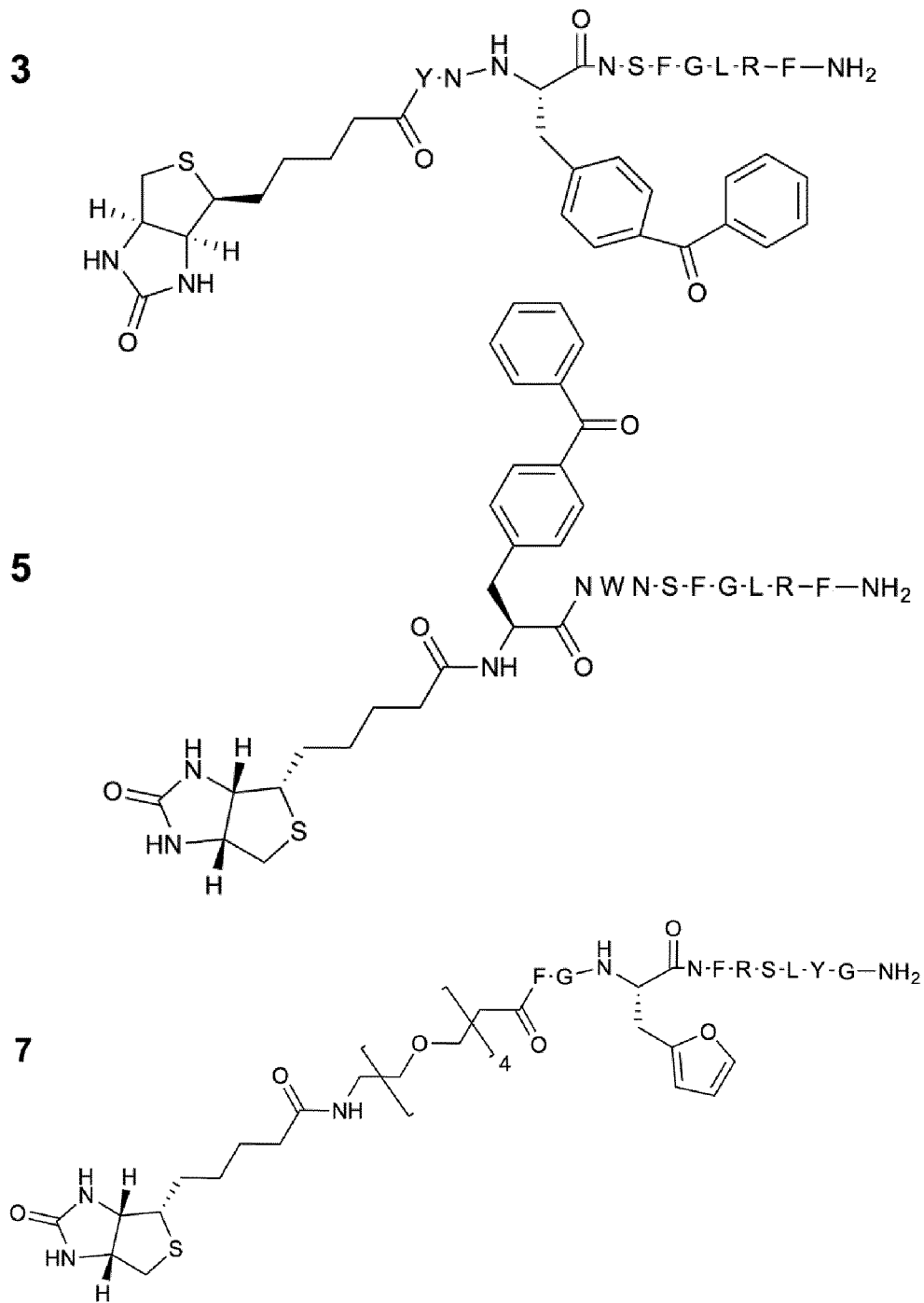

Compound 1 is the wildtype kisspeptin-10 peptide (FIG. 4). Previous alanine scans on kisspeptin-10 revealed the importance of the C-terminus for receptor binding. Based on these findings, a furan moiety was introduced in the N-terminal part: in peptides 2 and 4 Trp3 and Tyr 1 were respectively substituted by 2-furyl-L-alanine (FUA) (FIG. 4). By analogy, compounds 3 and 5 carry 4-benzoyl-L-phenylalanine (BPA) at these positions (FIG. 4). The N-termini of the peptides were biotinylated for easy detection. Compounds 2 to 5 had biotin directly coupled to the N-terminus. In compound 6, featuring an identical sequence as peptide 2, the N-terminus was separated from biotin by 4 polyethylene glycol (PEG) units (FIG. 4). Compound 7 is a randomized sequence version of compound 6, still containing a furan moiety at position 3 (FIG. 4).

The furan-peptides 2 to 6 were used in comparative methods for crosslinking a cell surface receptor and a ligand.

Comparative Example: Crosslinking Furan-Peptide Kisspeptin-10 and Cell Surface Receptor G-Protein Coupled Receptor GPR54 by Adding NBS as an Activation Signal or by Photoaffinity Crosslinking Comparative crosslinking experiments were performed with the kisspeptin-10 furan-peptides on MDA-MB-231 cells cultured in a confluent layer. Cells were cultured as described in Materials and methods, Cell culture. The cell medium was replaced with cold phosphate buffered saline (PBS) buffer prior to incubating the MDA-MB-231 cells with the furan-peptides (see Materials and methods, Crosslinking furan-peptides to cellular receptor in PBS). These are the same reaction conditions generally used for photocrosslinking on cells to prevent side-reactions as well as toxicity by heating upon irradiation.

Figure 6A:
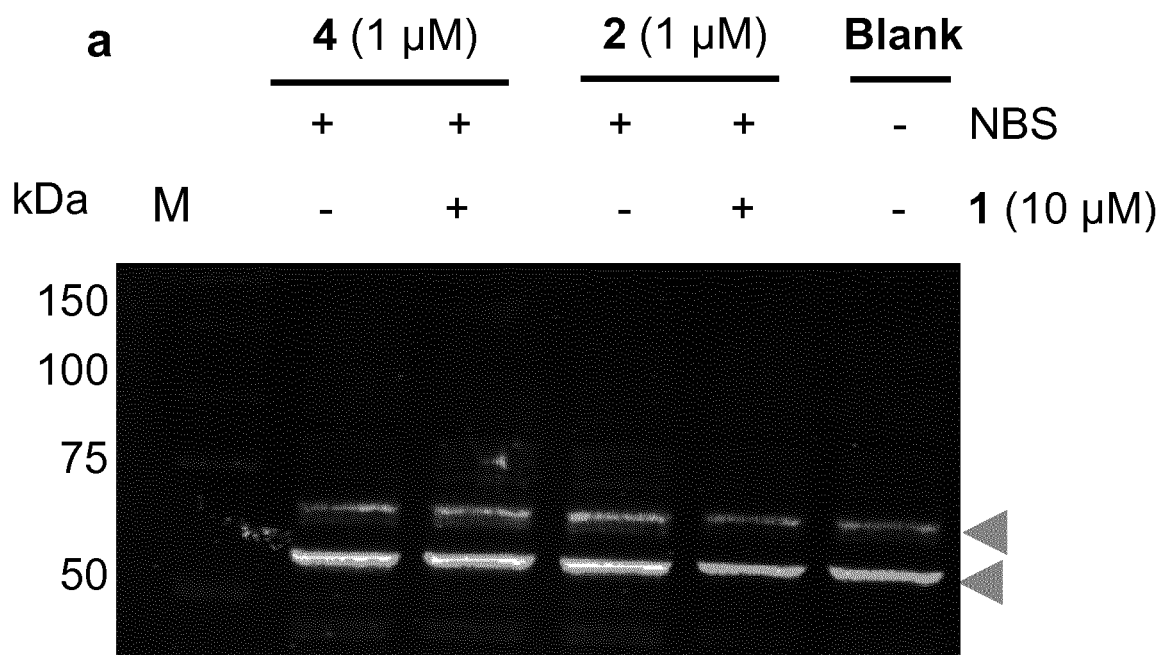
FIG. 6A represents a photograph of the Western blot using an antibody against GPR54.
Figure 6B:
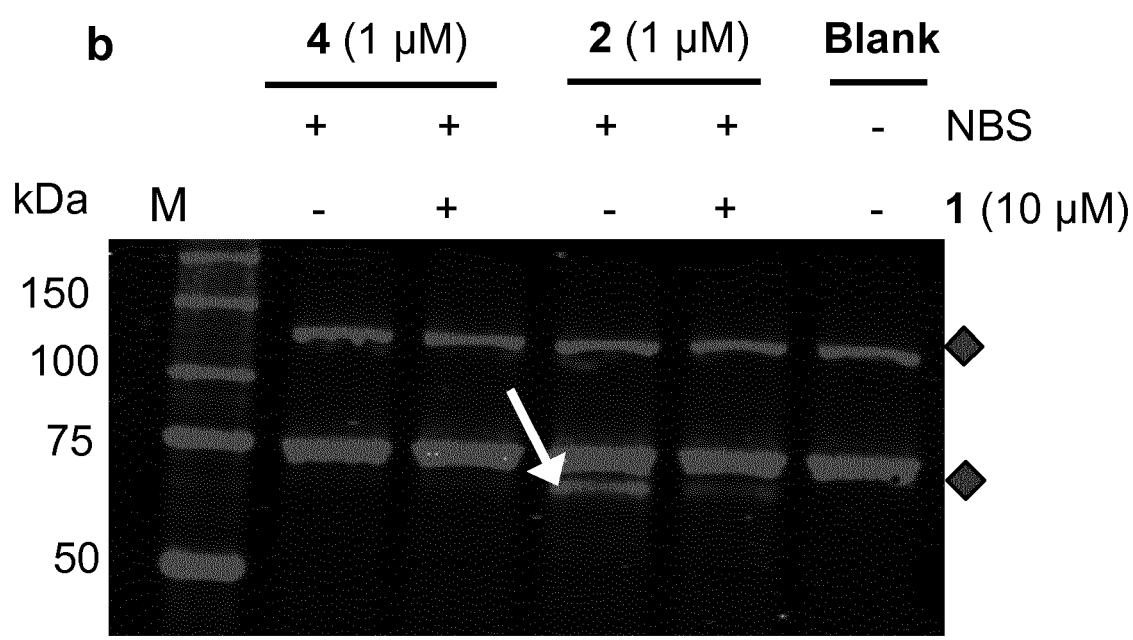
FIG. 6B represents a photograph of the same Western blot using biotin-responsive streptavidin.
Figure 7:
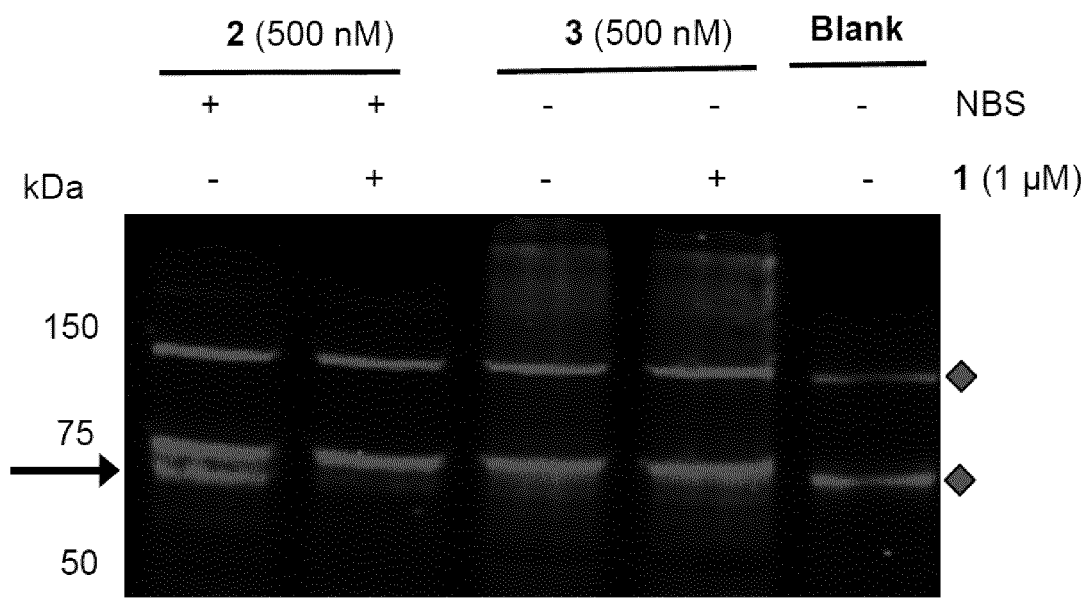
FIG. 7 represents a photograph of a Western blot illustrating cell surface receptor-ligand crosslink formation on living cells using comparative methods for crosslinking (using NBS as an activation signal or using photo-crosslinking). Western blot of cell lysates prepared after crosslinking furan-modified kisspeptin peptides on MDA-MB-231 cells. Biotinylated proteins are visualized. Blank shows the background signals from endogenously biotinylated carboxylases (75 and 130 kDa, diamonds). The position of the crosslinked biotinylated cell surface receptor-ligand complex is indicated by an arrow.

The MDA-MB-231 cells were incubated with peptides 2 and 4 for 1 h. Subsequently, NBS was added to initiate furan oxidation and induce crosslink formation via this oxidation. After reaction for 1 h, cell lysates were prepared for Western Blot analysis and visualization of the receptor and the covalently bound peptide-receptor complex (see Materials and methods, Cell lysis and Western Blot analysis) (FIG. 6 and FIG. 7). In FIG. 6A, blank shows the endogenous receptor signals (arrowheads). In FIG. 6B and FIG. 7, blank shows the background biotin signals from endogenously biotinylated carboxylases (75 and 130 kDa, diamonds).

Using furan peptide 2, the formation of a ligand-cell surface complex was observed (based on the biotin label on peptide 2) at approximately 72 kDa (FIG. 6B, lane 4, arrow; FIG. 7, lane 1), which was not the case for the blank experiment (FIG. 6B, blank; FIG. 7, blank). This cell surface receptor-ligand complex was visualized using fluorescent streptavidin binding the biotin on the peptide probe.

In order to verify the specificity of the covalent binding, a competition experiment was performed in which furan-peptide 2 was added to the cells simultaneously with a higher concentration of the wild type kisspeptin-10 peptide 1 (FIG. 6B, lane 5). This clearly reduced the crosslinking signal, confirming the formation of a specific covalent bond between the GPR54 receptor and furan-peptide 2. With furan-peptide 4 (FUA at position 1), the formation of a covalent bond could not be observed, neither in the absence or presence of competing WT-peptide (FIG. 6B, lanes 2 and 3).

A further comparative experiment was performed under comparable conditions for the benzophenone-modified kisspeptin peptides. The BPA-modified peptides 3 and 5 were incubated for 1 h (at the same concentration as peptide 2 and 4) with the cultured cells in cold PBS and the cells were irradiated with UV-light (360 nm) to initiate crosslinking (see Materials and methods, Crosslinking benzophenone-peptide to cellular receptor in PBS). Two independent experiments were performed. With peptide 3, only a faint and less discrete crosslink signal was visible at 72 kDa (FIG. 7, lane 3). The photo-crosslinking reaction was less efficient compared with furan-peptide 2, and more intense background signals were present (FIG. 7, lanes 3 and 4). Lower amounts of crosslinked species were formed upon competitive incubation of peptide 3 and an excess of wild type peptide 1 (FIG. 7, lane 4, and results not shown).

Example 2: Covalently Binding of Furan-Peptide Kisspeptin-10 and Cell Surface Receptor G-Protein Coupled Receptor GPR54 by Endogenous Activation According to an Embodiment of the Present Invention Furan is in se, an essentially stable, non-reactive moiety requiring oxidation to initiate crosslinking Therefore, previously, NBS was added to the cells with peptides as an activation signal to convert the furan moiety into an α-β unsaturated aldehyde for crosslink formation. Surprisingly, in a control experiment without any activation signal performed on living cells, the present inventors also observed a strong crosslinking signal. This indicated that the furan moiety was activated by oxidation in the cell culture, likely by an oxidative agent provided by the cells. The present inventors thus demonstrated for the first time chemical crosslinking of a modified ligand on its endogenous unmodified receptor in cells without any form of exogenous intervention (e.g., chemical activation signal, (UV-)light). The precise nature of the endogenous (cellular) oxidizing source is unknown.

Figure 8:
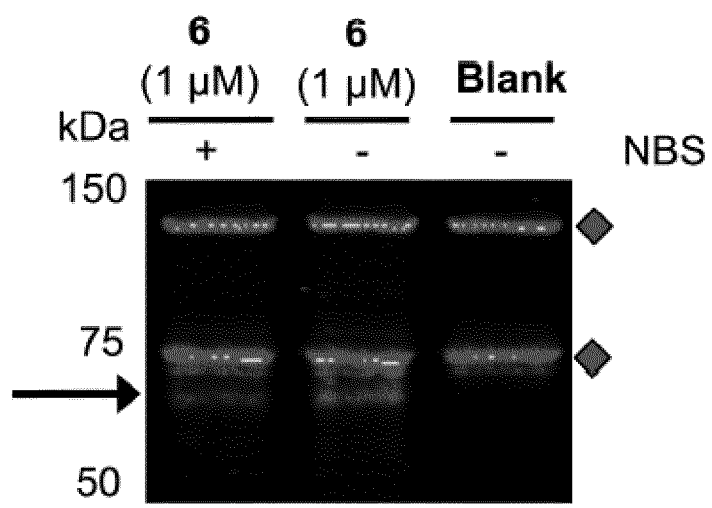
FIG. 8 represents a photograph of a Western blot illustrating covalent binding of a cell surface receptor and a ligand on living cells using a method according to an embodiment of the present invention (lane 2) and a comparative method (lane 1, with addition of NB S). Western blot of cell lysates prepared after covalently binding furan modified kisspeptin peptides on MDA-MB-231 cells in growth medium comprising 10% serum. Only the signal for biotin is shown. Blank shows the background signals from endogenously biotinylated carboxylases (75 and 130 kDa, diamonds). The position of the crosslinked biotinylated cell surface receptor-ligand complex is indicated by an arrow.
Figure 9A:
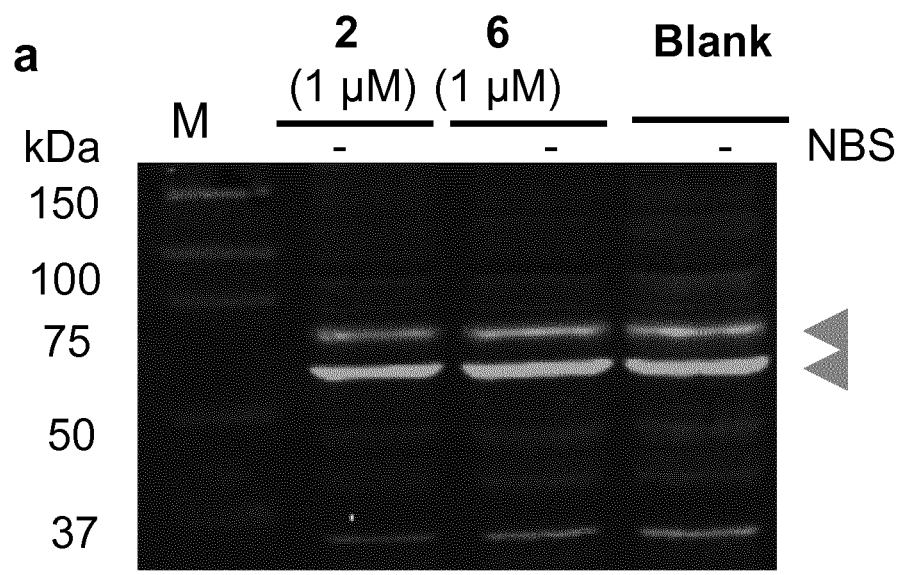
FIG. 9A represents a photograph of the Western blot using an antibody against GPR54.
Figure 9B:
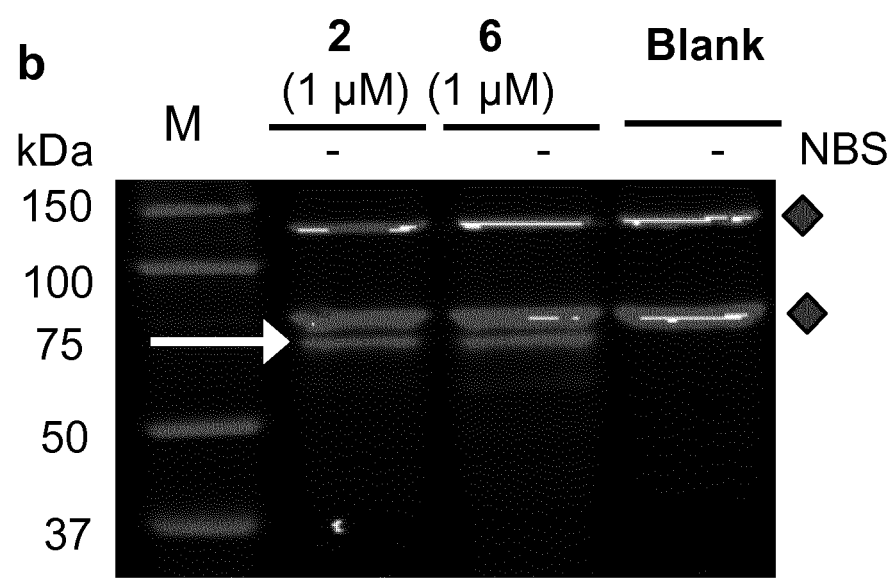
FIG. 9B represents a photograph of the same Western blot using biotin-responsive streptavidin. M: marker proteins.

A method for covalently binding a cell surface receptor and a ligand illustrating the present invention was performed as follows. Briefly, the crosslinking experiments were performed with the kisspeptin-10 furan-peptides in situ, on MDA-MB-231 cells cultured in a confluent layer. The method according to an embodiment of the present invention was performed by contacting the MDA-MB-231 cells with furan-peptide 6 under physiological conditions (normal growth medium containing 10% FBS and 37° C.) for 30 min (see Materials and methods, Crosslinking furan-peptides to cellular receptor in growth medium). After reaction, cell lysates were prepared for Western Blot analysis and visualization of the receptor and the covalently bound ligand-cell surface receptor complex (see Materials and methods, Cell lysis and Western Blot analysis). Using furan-peptide 6, the formation of a crosslink at approximately 72 kDa was observed (FIG. 8, lane 2, arrow), which was not the case for the blank experiment (FIG. 8, blank). The ligand-cell surface receptor complex was visualized using fluorescent streptavidin binding the biotin on the peptide probe. In FIG. 8, only the signal for biotin is shown. The efficiency of covalently binding of furan-peptide 6 was shown to be similar to that of furan-peptide 2 (FIG. 9B). Furan-peptide 6 contains a short polyethylene glycol linker of four units between the N-terminus and the biotin moiety. Efficiency of covalently binding of furan-peptide 6 was compared to that of furan-peptide 2 in medium comprising serum at 37° C. A slightly stronger signal of the covalent cell surface receptor-ligand complex was observed when using furan-peptide 6 (FIG. 9B). Better accessibility of the streptavidin to the biotin moiety due to less steric hindrance is a possible explanation for this finding. The 72 and 54 kDa subspecies of the GPCR54 receptor are shown in a FIG. 9A (arrowheads).

The covalently binding was also performed under the same conditions but with the addition of NBS as an activation signal (FIG. 8, lane 1). Higher efficiency was seen without addition of any exogenous activation signal to the medium (FIG. 8, compare lane 1 and lane 2). Hence, the method according to an embodiment of the present invention allows for efficient covalently binding of a cell surface receptor and a ligand without the need for any chemical or physical activation signal.

The molecular weight of the biotinylated covalently bound cell surface receptor-ligand complex indicates that the furan-peptide 6 mainly crosslinks to the membrane-presented, glycosylated receptor form (FIG. 5). This illustrates that the covalent binding of the kisspeptin-10 and GPR54 occurs in situ at the plasma membrane and thus at the site of the physiological ligand interaction.

Figure 10A:
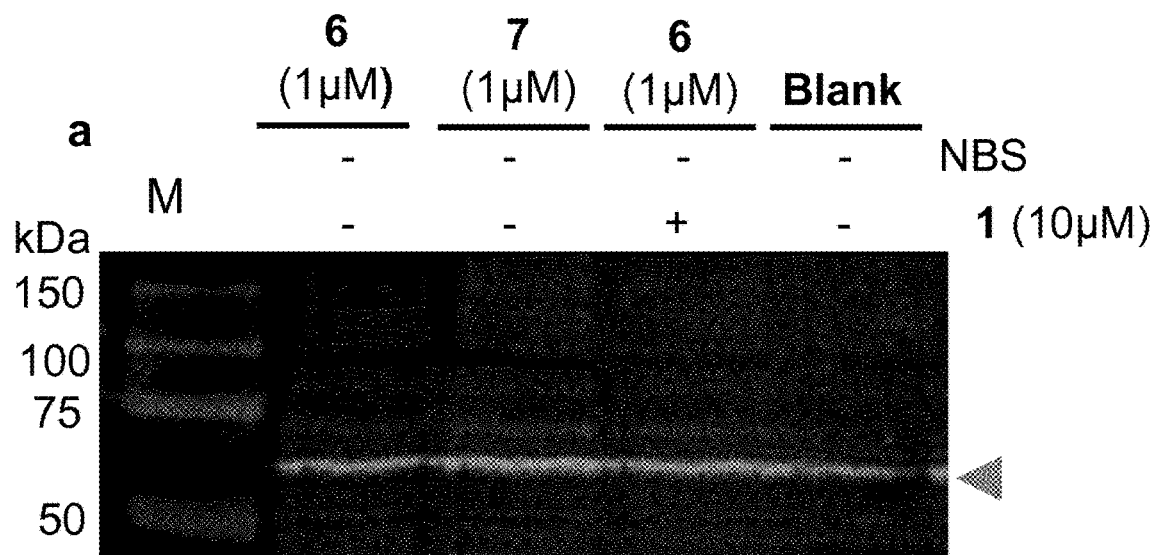
FIG. 10A represents a photograph of the Western blot using an antibody against GPR54.
Figure 10B:
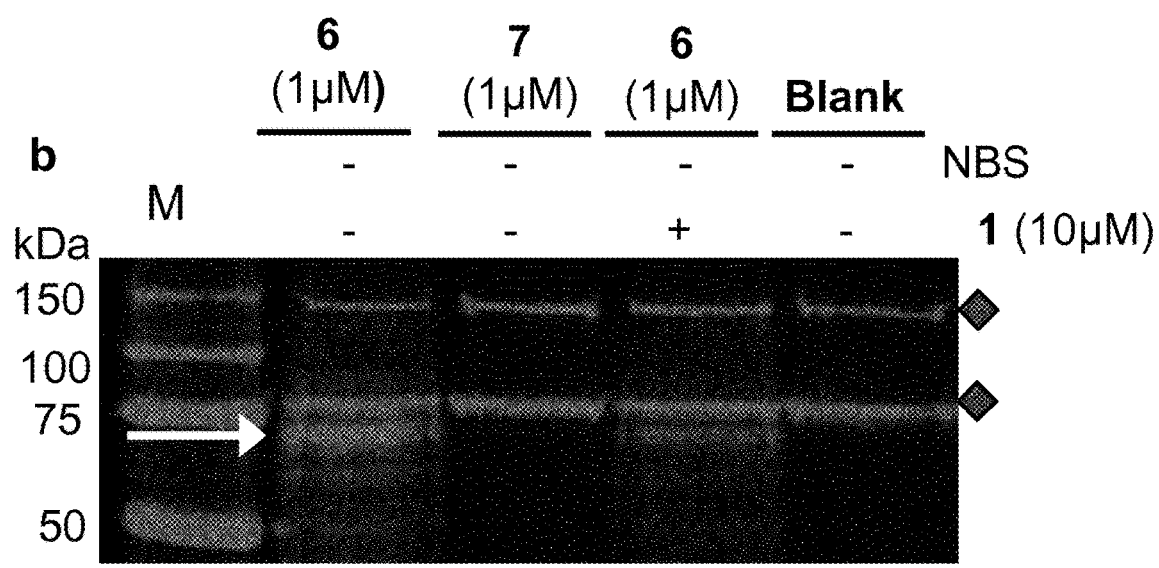
FIG. 10B represents a photograph of the same Western blot using biotin-responsive streptavidin. M: marker proteins.

To give final proof to the formation of a selective covalent bond using the method according to an embodiment of the present invention, we used furan-peptide 7, a random kisspeptin-10, with a furan moiety incorporated at the third position. Like furan-peptide 6, this peptide was biotinylated using a PEG(4)-linker at the N-terminus. Upon incubation, absolutely no crosslink signal was observed (FIG. 10B, lane 3). The 72 kDa form of the GPCR54 receptor is shown in a FIG. 10A (arrowheads).

The results thus illustrate that the method according to an embodiment of the present invention allows covalent binding upon specific binding of a ligand to its cell surface receptor.

Figure 12A:
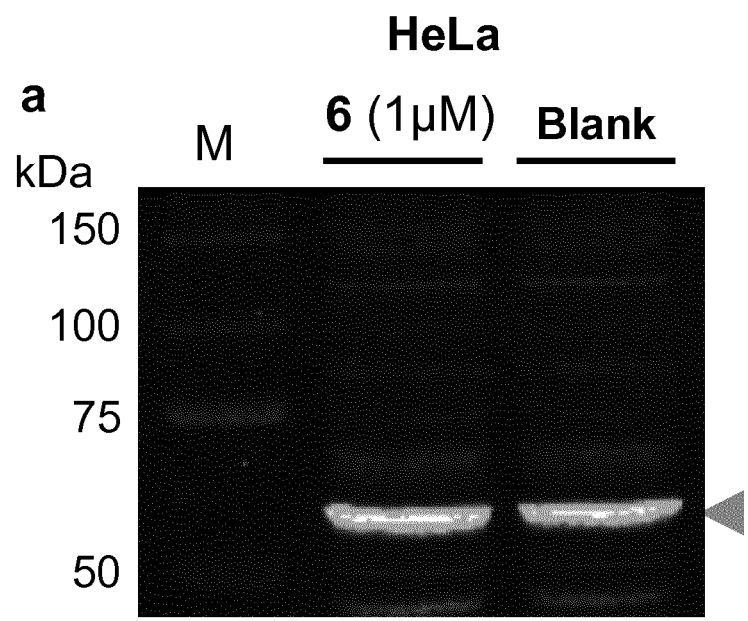
FIG. 12A represents a photograph of the Western blot using an antibody against GPR54.
Figure 12B:
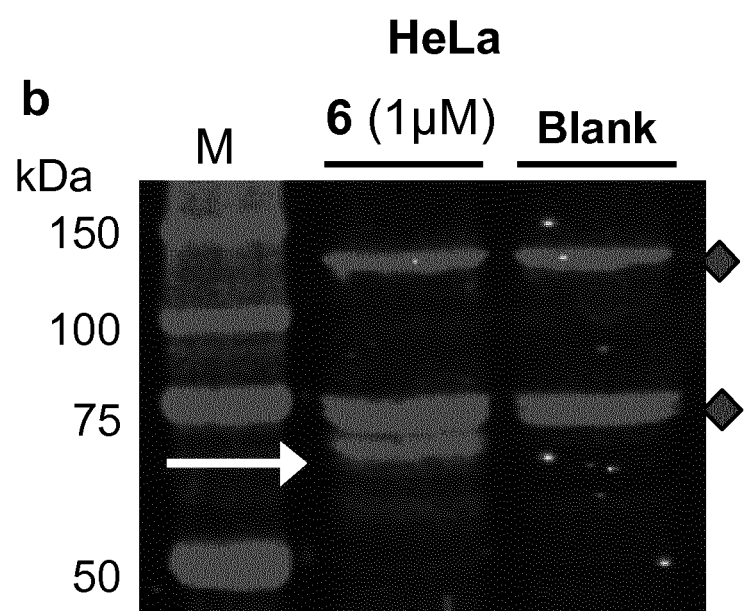
FIG. 12B represents a photograph of the same Western blot using biotin-responsive streptavidin. Arrow: cell surface receptor-ligand complex (about 72 kDa). Diamonds: biotinylated carboxylases (75 and 130 kDa); arrowhead: receptor GPR54. M: marker proteins.
Figure 13A:
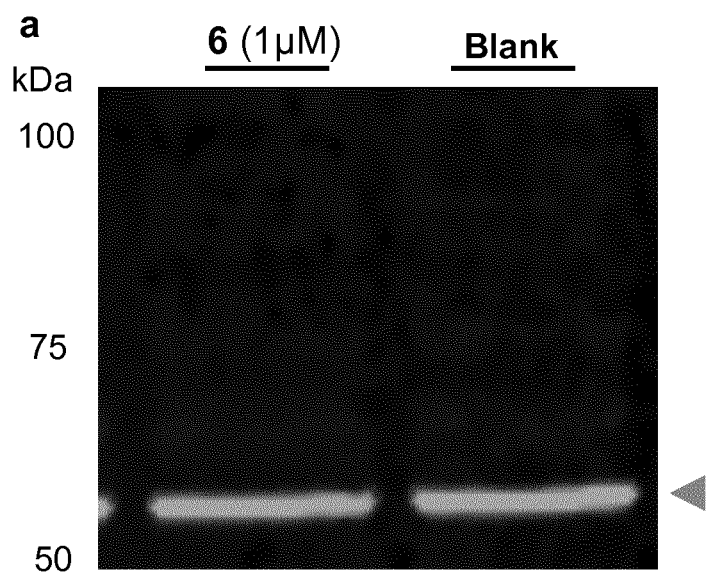
FIG. 13A represents a photograph of the Western blot using an antibody against GPR54.
Figure 13B:
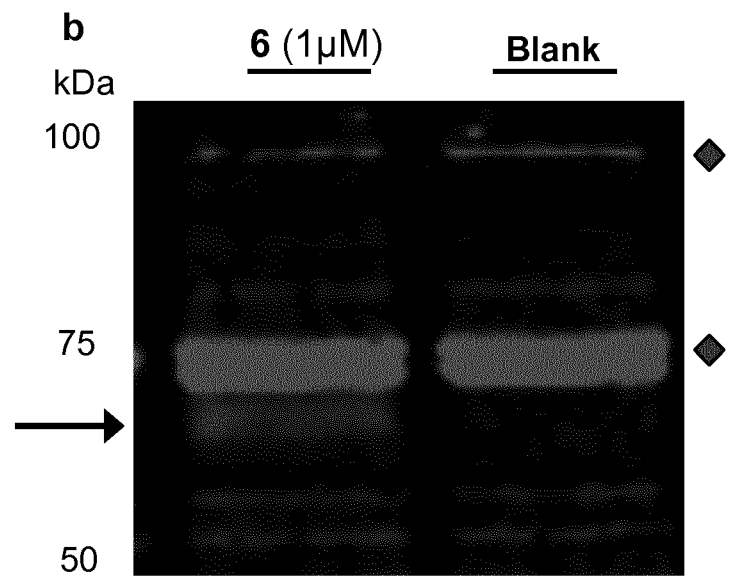
FIG. 13B represents a photograph of the same Western blot using biotin-responsive streptavidin. Arrow: cell surface receptor-ligand complex (about 72 kDa). Diamonds: biotinylated carboxylases (75 and 130 kDa); arrowhead: receptor GPR54. M: marker proteins.

Example 3: Covalent Binding of a Cell Surface Receptor and a Ligand Specifically Binding to the Cell Surface Receptor in Different Cell Lines According to Embodiments of the Present Invention To check the applicability of the method according to the present invention in different biological contexts, different cell lines expressing GPR54 receptor were used. In human cancer cell lines HeLa (FIG. 12A and FIG. 12B) and MCF-7 (FIG. 13A and FIG. 13B), efficient crosslinking of furan-peptide 6 and GPR54 was achieved upon incubating the living cells with furan-peptide 6 (FIG. 12B and FIG. 13B, respectively, arrow). MDA-MB-231, HeLa and MCF-7 are all human breast cancer cell lines. Furthermore, it was tested whether the covalent binding was also observed using normal cell lines, for example cells lines derived from non-diseased such as non-cancerous or non-infected tissue or cells.

Figure 11A:
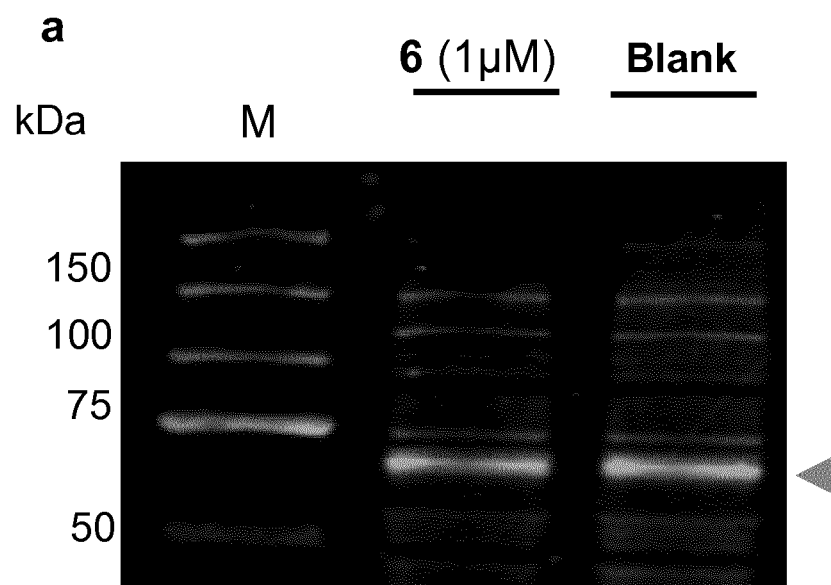
FIG. 11A represents a photograph of the Western blot using an antibody against GPR54.
Figure 11B:
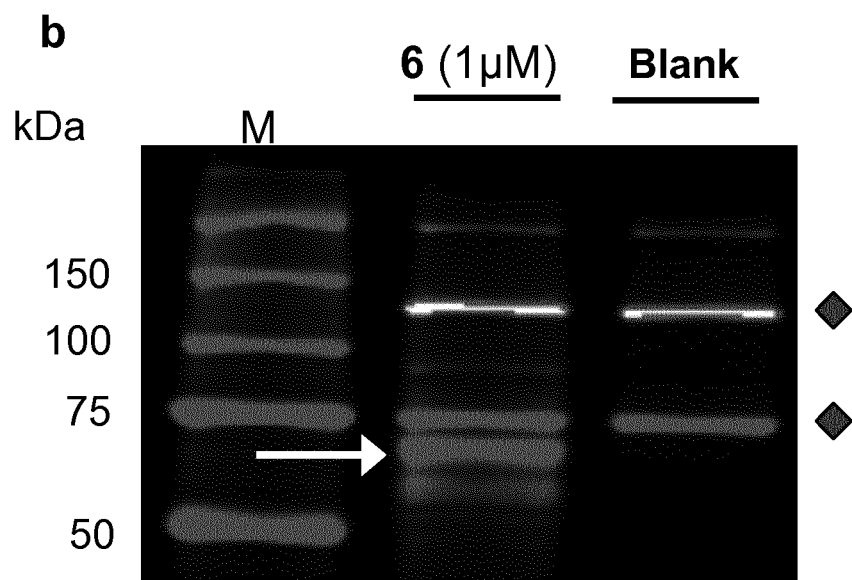
FIG. 11B represents a photograph of the same Western blot using biotin-responsive streptavidin. Arrow: cell surface receptor-ligand complex (about 72 kDa). Diamonds: biotinylated carboxylases (75 and 130 kDa); arrowhead: receptor GPR54. M: marker proteins.

In mouse fibroblast NIH 3T3 cell line, covalent binding of furan-peptide 6 and GPR54 was also efficiently achieved upon incubation of the living cells with furan-peptide 6 (FIG. 11B, crosslink indicated by arrow). In all tested cell lines, no exogenous intervention such as NBS treatment was needed for the formation of the covalent bonds. Interestingly, in NIH 3T3, the inherent relative abundance of the different receptor species is very different: the GPR54 signal at 54 kDa was barely visible (FIG. 11A) in contrast to a very strong band at 72 kDa (FIG. 11B). As the furan modified kisspeptin-10 peptide preferably crosslinks with this 72 kDa receptor form, a very strong crosslinking signal was observed (FIG. 11B, lane 2).

Figure 14A:
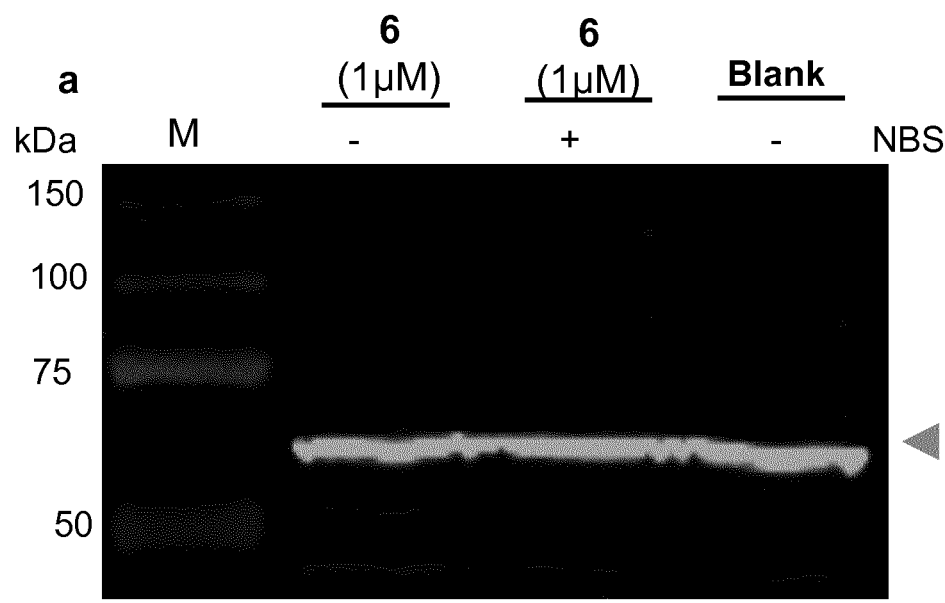
FIG. 14A represents a photograph of the Western blot using an antibody against GPR54.
Figure 14B:
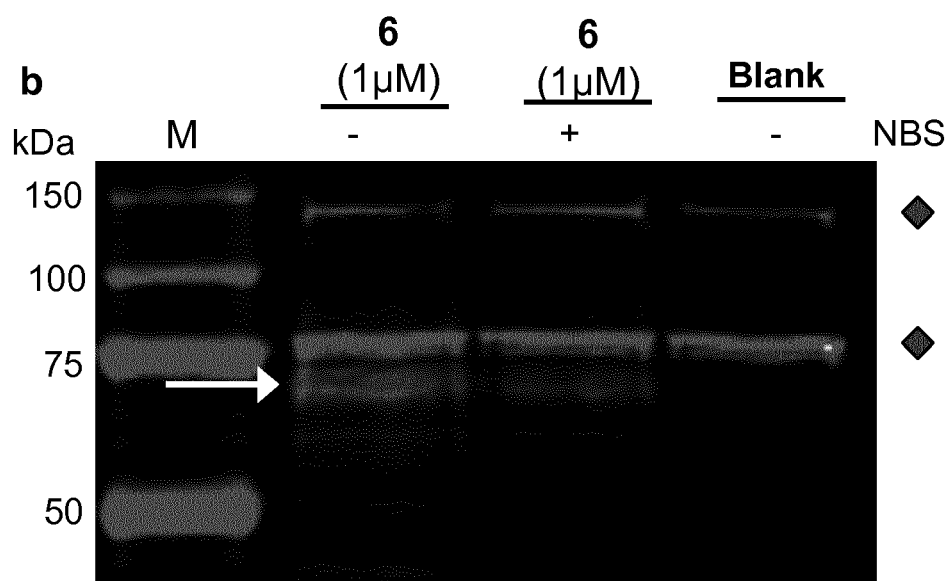
FIG. 14B represents a photograph of the same Western blot using biotin-responsive streptavidin. Arrow: cell surface receptor-ligand complex (about 72 kDa). Diamonds: biotinylated carboxylases (75 and 130 kDa); arrowhead: receptor GPR54. M: marker proteins.

Finally, the human embryonic kidney cell line, HEK-myc-KISS1R, that stably expresses relatively low levels of myc-tagged GPR54 was used. Furan-peptide 6 was tested with the addition of NBS and without the addition of any activation signal (FIG. 14A and FIG. 14B). In both conditions, covalent binding to the cell surface receptor GPR54 was observed (FIG. 14B), but the crosslink was stronger when no activation signal was added (FIG. 14B, compare lanes 2 and 3).

Example 4: Covalent Binding of a Cell Surface Protein and a Ligand Specifically Binding to the Cell Surface Protein In Vivo According to an Embodiment of the Present Invention To test the applicability of the method according to the present invention in vivo, MDA-MB-231 cells are injected subcutaneously into mice (three groups of n=3). When tumours reach a size of around 250-500 mm$^3$ (estimated after approximately 10-15 days), injections in the tumour are performed (intra-tumour injection) with the furan-kisspeptin peptide 6 (FIG. 4) (group 1, n=3), with peptide 7 (FIG. 4) (group 2, n=3), or a mock injection is performed (group 3, i.e. control group, n=3). Peptide 7 is a randomized sequence version of peptide 6 still containing a furan moiety at position 3. The peptide concentration in the injected physiological buffer is minimally 1 μM. To estimate the maximal peptide concentration, toxicity tests are performed on cultured cells in vitro using peptide 6 and 7, and acute local toxicity tests are performed using subcutaneous injection of peptide 7 in mice. The injected peptides 6 and 7 also comprise biotin (FIG. 4) to allow detection for instance by Western blot analysis. The peptides may further comprise a fluorescent agent for immunohistochemistry. Several hours after injection, the tumour is isolated, proteins are extracted from the tumour tissue, and covalent binding of the kisspeptin peptide to its cell surface receptor GPR54 is analysed by Western blot analysis. Covalent binding of the cell surface protein (GPR54) to the ligand (kisspeptin peptide) is detected. Alternatively, the tumour tissue is prepared for immunohistochemistry.

Example 5: Covalent Binding of a Cell Surface Protein and a Ligand Specifically Binding to the Cell Surface Protein According to an Embodiment of the Present Invention to Allow In Situ Visualization of the Cell Surface Protein on Adherent Cells In order to study the dynamics of a cell surface receptor such as C—X—C chemokine receptor type 4 (CXCR4) in the cell membrane, a set of CVX15 peptides is synthesized, each carrying one furan moiety at a different position within the sequence. CVX15 is a peptide antagonist of the G-protein coupled receptor CXCR4. CVX15 is a 16-residue cyclic peptide characterized as an HIV-inhibiting and anti-metastatic agent and its binding site on the CXCR4 receptor has been determined (Wu et al, 2010, Science, 330, 1066-71). When synthesizing the set of CVX15 peptides, each carrying one furan moiety at a different position within the sequence; the choice of positions can be guided by the information of the known binding site. The furan-containing CVX15 peptides are in addition tagged with a fluorescent moiety which is not interfering with binding.

Adherent living MDA-MB-231 cells (e.g., $5 \times 10^5$ cells) are incubated in cell culture medium with each of the different furan-containing CVX15 peptides (concentration between 0.1-5 µM) to allow crosslinking Using confocal microscopy on fixed cells, the furan-containing CVX15 peptide that most efficiently crosslinks to CXCR4, is selected for further experiments. Subsequently, living MDA-MB231 cells are contacted with the selected furan-containing CVX15 peptide (i.e., a first furan-containing CVX15 peptide containing a fluorescent moiety) to covalently bind the peptide to CXCR4 on the cell surface. After washing away unbound furan-containing CVX15 peptide, the dynamics of the CXCR4 receptor on the cell surface is visualized and recorded using live cell imaging via the fluorescent moiety coupled to the furan-containing CVX15 peptide. In addition, the selected furan-containing CVX15 peptide is synthesized but carrying a different fluorophore (i.e., a second furan-containing CVX15 peptide). MDA-MB cells are contacted with a mixture of the first and second furan-containing CVX15 peptides, each carrying a different fluorophore, thereby obtaining CXCR4 receptors covalently bound to CVX15 peptides carrying different fluorophores. CXCR4 receptor clustering on the cell surface of living MDA-MB-231 cells is detected based on co-localization of the two fluorophore signals.

Example 6: Covalent Binding of a Cell Surface Protein and a Ligand Specifically Binding to the Cell Surface Protein According to an Embodiment of the Present Invention to Allow In Situ Visualization of the Cell Surface Protein on Cells in Suspension A set of furan-containing CVX15 peptides is prepared as described in Example 5. A Jurkat cell line (i.e., T-cell cell line growing in suspension culture) is used. Living Jurkat cells ($1 \times 10^5$ cells) are contacted with each of the different furan-containing CVX15 peptides (concentration between 0.1-5 µM) to allow covalent binding. In order to allow imaging, the cells are embedded in a small volume (e.g. 20-40 µl) of a hydrogel composed of extracellular matrix proteins (e.g., collagen type I). The furan-containing CVX15 peptide that most efficiently crosslinks to CXCR4 is selected using confocal microscopy on fixed cells. Next, living Jurkat cells are contacted with the selected furan-containing CVX15 peptide to form the fluorescent ligand-receptor covalently bound complex. The cells are then embedded in a small volume (20-40 µl) of a hydrogel composed of extracellular matrix proteins (e.g. collagen type I) to allow imaging. The dynamics of the CXCR4 receptor, covalently bound to the fluorescent CVX15 ligand, on the cell surface is visualized and recorded using live cell imaging. In addition, the selected furan-containing CVX15 peptide is synthesized but carrying a different fluorophore (i.e., a second furan-containing CVX15 peptide). Jurkat cells are contacted with a mixture of the first and second furan-containing CVX15 peptides, each carrying a different fluorophore, thereby obtaining CXCR4 receptors covalently bound to CVX15 peptides carrying different fluorophores. CXCR4 receptor clustering on the cell surface of living Jurkat cells is detected based on co-localization of the two fluorophore signals.

Example 7: Covalent Binding of a Cell Surface Protein and a Ligand Specifically Binding to the Cell Surface Protein According to an Embodiment of the Present Invention to Allow In Situ Visualization of the Cell Surface Protein In order to study the dynamics of a cell surface receptor such as C—C chemokine receptor type 5 (CCR5) in the cell membrane, a set of Maraviroc compounds is synthesized, each carrying one furan moiety at a different position. Maraviroc is a small molecule antagonist of the CCR5 cell surface receptor. The Maraviroc binding site on the CCR5 receptor has been determined (Tan et al., 2013, Science, 341, 1387-90). By chemical synthesis, a set of Maraviroc compounds is generated, each compound comprising a fluorescent moiety and carrying one furan moiety at a different position. The choice of positions is guided by the information of the known binding site. Living cells ($1 \times 10^5$ cells) of the Jurkat cell line in suspension culture are incubated, each with a Maraviroc compound (concentration e.g. between 0.1-10 µM) to allow crosslinking. To allow imaging, the cells are embedded in a small volume (e.g. 20-40 µl) of hydrogel composed of extracellular matrix proteins (e.g. collagen type I). The furan-containing Maraviroc compound that most efficiently crosslinks to the cell surface receptor, is selected using confocal microscopy on fixed cells. Subsequently, living Jurkat cells are contacted with the selected furan-containing Maraviroc compound to form the fluorescent ligand-receptor covalently bound complex. The cells are embedded in a small volume (20-40 µl) of hydrogel composed of extracellular matrix proteins (e.g. collagen type I) in order to allow imaging. The dynamics of the CCR5 receptor, covalently bound to the fluorescent Maraviroc ligand, on the cell surface is visualized and detected using live cell imaging.

Example 8: Cell-Based Assay for Identifying for an Orphan Ligand a Cell Surface Protein being Capable of Specifically Binding to the Ligand According to an Embodiment of the Present Invention A cell-based assay is performed to identify the cell surface protein for an orphan ligand, such as the alpha fetoprotein peptide (AFPep) ligand (also called growth inhibitory protein 8 or GIP-8). This peptide ligand is a 9-mer circularized variant of an 8-mer peptide derived from alpha fetoprotein (AFP). AFPep activities in vitro and in vivo include specific effects on estrogen receptor (ER) positive cancer cells. The receptor of AFPep ligand is unknown. Variants of the 9-mer AFPep, and of its non-circular 8-mer peptide, carrying one furan moiety (either at the N- or C-terminus or at an internal position) and a label for detection (e.g., biotin) are synthesized. Living ER-positive breast cancer cell line MCF-7 cells ($5\times10^6$ cells) are contacted with each of these peptides (e.g. at 0.5 to 2 µM) in cell medium. The ER-negative cell line MDA-MB-231, for which it is known that AFPep causes no growth inhibitory effects, and thus anticipated not to express the unknown cell surface receptor, is used as negative control. The cells are harvested, lysed, and analysed using Western Blotting with an antibody against the label to detect the presence of a covalently bound complex in which the peptide ligand is specifically bound to a cell surface protein. Mass spectrometry analysis is used to identify the cell surface receptor covalently bound to AFPep.

Example 9: Cell-Based Assay for Identifying a Binding Site of a Cell Surface Protein and a Ligand Specifically Binding the Cell Surface Protein According to an Embodiment of the Present Invention A cell-based assay is performed to identify a binding site of a cell surface protein and a ligand such as the alpha fetoprotein peptide (AFPep) ligand, as described in Example 8. Variants of the non-circular 8-mer peptide variant of AFPep carrying one furan moiety and a biotin label are used to identify the binding site. Living ER-positive breast cancer cell line MCF-7 cells ($5\times10^6$ cells) are contacted with these peptides (e.g. at 0.5 to 2 µM) in cell medium. The ER-negative cell line MDA-MB-231, for which it is known that the AFPep causes no growth inhibitory effects, and is thus anticipated not to express the receptor, is used as negative control. The cells are harvested, lysed, and analysed using Western Blotting using an antibody against the label to determine the presence of a covalently bound complex in which the peptide ligand is specifically bound to a cell surface protein. The presence of a covalently bound complex identifies the amino acid comprising a furan moiety as being part of the binding site of the cell surface protein and the peptide. In addition or alternatively, mass spectrometry analysis is used to identify the covalently bound cell surface receptor of AFPep and eventually to confirm the binding site.

Figure 15:
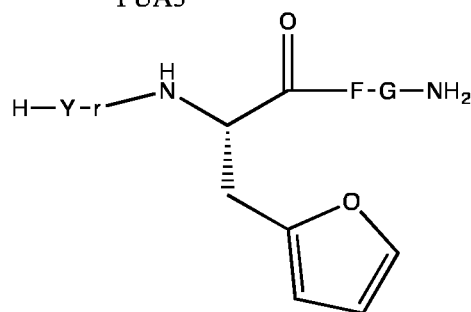
FIG. 15 represents an overview illustrating the sequence, chemical formula, exact mass, and molecular weight of opioid peptides and furan-modified analogues thereof.
Figure 15:
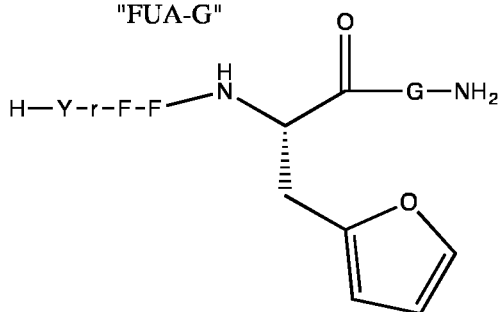
Figure 15:
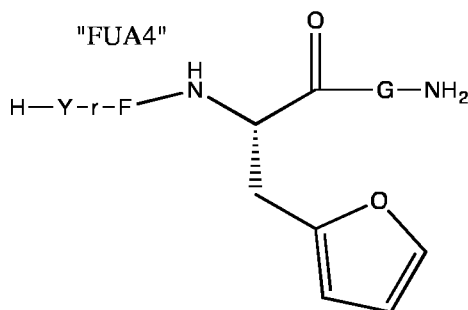

Example 10: Cell-Based Assay for Identifying for an Opioid Peptide, the Opioid Receptor (Subtype) Capable of Specifically Binding to the Opioid Peptide According to an Embodiment of the Present Invention A first goal of this experiment was the synthesis of a furan-modified opioid peptide (e.g. receptor agonist peptide). As the N-terminus of the opioid peptide (H—Y-r-F—F—NH$_2$ with r=d-Arginine) (FIG. 15, wild type peptide or "WTP") is known to be crucial for binding with the opioid receptor, the C-terminus of the peptide (i.e. C-terminal amide) was chosen for modification. A furan moiety directly at the C-terminus may give rise to a more troublesome synthesis, and for that reason an extra glycine was attached to the C-terminus as linker (FIG. 15, "WTP-G"). Different opioid peptide analogues were produced to be tested for their ability to bind the opioid receptor (FIG. 15, "FUA3", "FUA-G", and "FUA4").

Next, the synthesised peptides were subjected to biological activity testing, to know whether they still bind to the opioid receptor. If so, it is tested to which opioid receptor subtype they bind. It is also investigated whether the opioid peptides behave as agonist or antagonist. The following assays are performed: radio-ligand binding assay, $^{35}$S GTP binding assay, and tissue experiments, including guinea pig ileum (GPI) and mouse vas deferens (MVD) tests.

TABLE 1

| Opioid receptor binding affinities of irreversible orthosteric ligands to the human opioid receptors (CHO-hOR cells) | |
|---|---|
| Peptide | Binding affinity $K_i$ (nM) ± SEM µ-opioid receptor (MOR) |
| WTP-G | 5.84 ± 1.29 |
| WTP | 8.04 ± 0.44 |
| FUA3 | 32.6 |
| FUA-G | 145 |
| FUA4 | 251 |

Based on these results, the binding of the furan-modified peptide FUA3 was acceptable. Further biological assays are performed.

The furan-modified opioid peptides that bind to opioid receptors are chosen for further crosslinking experiments. Cells overexpressing an opioid receptor subtype are incubated with the furan-modified opioid peptides without the addition of an exogenous activation signal, illustrating an embodiment of the invention. Crosslinking with the opioid receptor subtypes is evaluated by Western blotting. If crosslinking is successful, the crosslinked complex can be used to elucidate the opioid peptide-opioid receptor complex.

The invention claimed is:

1. A method for covalently binding a cell surface protein and a ligand, the ligand being capable of specifically binding to the cell surface protein, the method comprising contacting living cells expressing the cell surface protein with the ligand comprising at least one furan moiety without the addition of an exogenous activation signal, thereby covalently binding the cell surface protein and the ligand.

2. The method according to claim 1, wherein the cell surface protein is selected from the group consisting of a cell surface receptor, a cell adhesion molecule, and a cell surface protease.

3. The method according to claim 1, wherein the cell surface protein is a cell surface receptor selected from the group consisting of a G-protein coupled receptor (GPCR), an immune receptor, an ion channel-linked receptor, and an enzyme-linked receptor preferably wherein the cell surface protein is a GPCR.

4. The method according to claim 1, wherein the ligand is a peptide, a nucleoside, a nucleic acid, a lipid, a polysaccharide, a small molecule, or a combination thereof, preferably wherein the ligand is a peptide.

5. The method according to claim 1, wherein the cell surface protein is a GPCR and the ligand is a peptide.

6. The method according to claim 1, wherein the furan moiety of the ligand is oxidized by endogenous activation.

7. The method according to claim 6, wherein the endogenous activation occurs at the extracellular space of the cell membrane.

8. The method according to claim 1, wherein the cell surface protein comprises at least one amine group, hydroxyl group, sulfhydryl group, imidazole group and/or indole group.

9. The method according to claim 6, wherein the oxidized furan moiety of the ligand reacts with the amine group, hydroxyl group, sulfhydryl group, imidazole group and/or indole group of the cell surface protein.

10. The method according to claim 1, wherein the method is performed under physiological conditions.

11. The method according to claim 1, wherein the living cells are normal cells.

\* \* \* \* \*